(12) United States Patent
Torrens-Jover et al.

(10) Patent No.: US 7,041,665 B2
(45) Date of Patent: *May 9, 2006

(54) BENZOXAZINONE DERIVATIVES, THEIR PREPARATION AND USE AS MEDICAMENTS

(75) Inventors: Antonio Torrens-Jover, Barcelona (ES); Jose Aurelio Castrillo-Perez, Barcelona (ES); Jordi Frigola-Constansa, Barcelona (ES)

(73) Assignee: Laboratories del Dr. Esteve, S.A., (ES)

( * ) Notice: Subject to any disclaimer, the term of this patent is extended or adjusted under 35 U.S.C. 154(b) by 0 days.

This patent is subject to a terminal disclaimer.

(21) Appl. No.: 10/409,235

(22) Filed: Apr. 8, 2003

(65) Prior Publication Data

US 2004/0067941 A1    Apr. 8, 2004

(30) Foreign Application Priority Data

Apr. 9, 2002    (ES) ................................ 200200813

(51) Int. Cl.
  *C07D 413/04*    (2006.01)
  *C07D 413/12*    (2006.01)
  *A61K 31/5365*   (2006.01)

(52) U.S. Cl. ..................... 514/230.5; 544/92
(58) Field of Classification Search ............... 544/92; 514/230.5
   See application file for complete search history.

(56) References Cited

U.S. PATENT DOCUMENTS 5,665,719 A * 9/1997 Bock et al. ............ 514/227.8

2004/0058920 A1 * 3/2004 Jover et al. ............ 514/230.5

OTHER PUBLICATIONS

Chronwall et al. Peptides 25 (2004) 359-363.*

* cited by examiner

*Primary Examiner*—Mark L. Berch
*Assistant Examiner*—Kahsay Habte
(74) *Attorney, Agent, or Firm*—Michael Best & Friedrich LLP

(57) ABSTRACT

The present invention relates to new compounds of general formula (I), as well as to their physiologically acceptable salts, the procedures for their preparation, the intermediate compounds for obtaining them, the application of the compounds of general formula (I) as medicaments in the prevention and treatment of disorders of the Central nervous System and to the pharmaceutical compositions containing them.

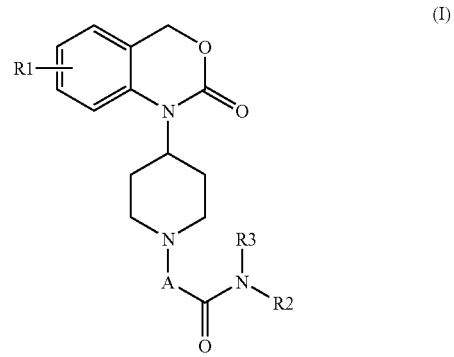

(I)

3 Claims, No Drawings

BENZOXAZINONE DERIVATIVES, THEIR PREPARATION AND USE AS MEDICAMENTS

FILED OF THE INVENTION

The present invention relates to new compounds of general formula (I), as well as to their physiologically acceptable salts, their preparation procedures, their application as medicinal products in human and/or veterinary therapeutics, and the pharmaceutical compositions that contain them.

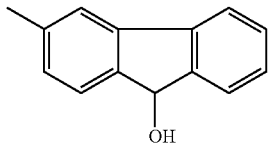

The new compounds object of the present invention may be used in the pharmaceutical industry as intermediate products and for the preparation of medicinal products.

BACKGROUND OF THE INVENTION

Neuropeptide Y (NPY), first isolated in porcine brain extracts (Tatemoto et. al. *Nature* 1982, 296, 659), is a 36-aminoacid peptide belonging to the family of pancreatic polypeptides, and is one of the most abundant peptides in the brain and in the central nervous system. In addition, NPY is also distributed in several parts of the peripheral nervous system.

Several studies suggest a significant role of NPY in food ingestion regulation and particularly in food dysfunctions like obesity, anorexia and bulimia. Specifically, NPY is a powerful stimulant of food ingestion. Thus, appetite is significantly increased when NPY is injected directly into the CNS of satiated mice (Clark J. T. et. al. *Endocrinology* 1984, 115, 427; Levine A. S. et. al. *Peptides* 1984, 5, 1025; Stanley B. G. et. al. *Life Sci*. 1984, 35, 2635; Stanley B. G. et. al. *Proc. Nat. Acad. Sci. USA* 1985, 82, 3940). On the other hand, NPY may play a role in cognitive function regulation, e.g. memory (Flood J. F. et. al. *Brain Res*. 1987, 421, 280; Redrobe J. P. et. al. *Brain Res*. 1999, 848, 153), and be active in anxiety (Heilig M. et. al. *Reg. Peptides* 1992, 41, 61) and depression (Heilig M. et. al. *Eur. J. Pharmacol*. 1988, 147, 465) processes.

NPY is also distributed in the peripheral system. Some studies suggest that it might be involved in hypertensive (Michel M. C: et. al. *J. Hypedtens*. 1995, 13, 153), and analgesic (Gehlert D. R. *Life Sci*. 1994, 55, 551) processes, among others.

The endogenous proteins that constitute NPY-binding receptors have been widely studied. Several have been cloned and expressed. At present, six different receptor subtypes, named Y1 to Y6, are recognized (Hispkind P. A. et. al. *Annu. Rep. Med. Chem*. 1996, 31, 1; Grunemar L. et. al. *TiPS Reviews*, 15,153). Each NPY receptor subtype is generally associated to a different biological activity. For example, Y2 receptor is involved in the induction of convulsions in rats (Dumont Y. et. al. *Brit. J. Pharmacol*. 2000, 129, 1075).

The most recently identified receptor is Y5 (Hu et. al. *J. Biol. Chem*. 1996, 271, 26315). There is evidence that Y5 receptor has a unique pharmacological profile related to food ingestion as compared to the other receptor subtypes. The fact that [D-Trp$^{32}$]NPY peptide, a selective Y5-receptor agonist with no affinity for Y1 receptor, stimulates food ingestion in rats (Gerald C. et. al. *Nature*, 1996, 382, 168), supports the hypothesis that Y5 receptor is related to exaggerated food consumption. Consequently, compounds antagonizing Y5 receptor should be effective to inhibit food ingestion and very useful to control diseases like obesity, or nutritional disorders like bulimia or anorexia.

Several NPY5 non-peptidic antagonists have been described. Thus, 2-aminoquinazoline derivatives [PCT Int. Appl. WO 9720823, 1997 (Novartis AG)], sulfonamides [PCT Int. Appl. WO 9719682, 1997 (Synaptic Pharmaceutical Corp.)], pyrazoles [PCT Int. Appl. WO 9824768, 1998 (Banyu Pharmaceutical Co., Ltd)], aminopyridines [PCT Int. Appl. WO 9840356, 1998 (Banyu Pharmaceutical Co., Ltd)], N-aralkyl-2-tetralinamines [PCT Int. Appl. WO 0020376, 2000 (Ortho McNeil Pharmaceutical Inc.)], several amides [PCT Int. Appl. WO 9835957, 1998 (Bayer Corp.)], pyridine and pyrimidine derivatives [PCT Int. Appl. WO 9940091, 1999 (Amgen Inc.)], carbazoles [PCT Int. Appl. WO 0107409, 2001 (Astra Zeneca AB.)], and spiroisoquinolinones [PCT Int. Appl. WO 0113917, 2001 (Bristol-Myers Squibb Co.)], have been prepared.

Benzoxazinone derivatives having biological activity related to NPY receptors are not described in any published work. The only background of benzoxazinone derivatives with biological activity disclosed in literature refer to P2X7-receptor antagonists, useful for the treatment of inflammatory, immune or cardiovascular diseases [PCT Int. Appl. WO 01044213, 2001 (Astrazeneca AB)], to oxytocin receptor antagonists, useful in tocology [PCT Int. Appl. WO 9725992, 1997 (Merck Co., Inc.)], to α1c adrenergic receptor antagonists [PCT Int. Appl. WO 9528397, 1995 (Merck Co., Inc.)], or to pharnesilproteintransferase enzyme inhibitors [PCT Int. Appl. WO 9738665, 1997 (Merck Co., Inc.)].

Painstaking research has led the investigators to synthesize new compounds of general formula (I) with interesting biological properties which render them particularly useful for application in human and/or veterinary therapeutics to treat diseases for which no similar compound has been previously claimed.

DETAILED DESCRIPTION OF THE INVENTION

The present invention comprises a series of benzoxazinone derivatives, the pharmaceutical formulations containing them and the synthesis intermediates used for their preparation. The compounds object of the invention are ligands of the receptor of the Y neuropeptide Y5 (NPY5), a receptor associated to several dysfunctions of the central and peripheral nervous systems, as well as of the cardiovascular system, and therefore useful in the manufacture of a medicinal product to prevent or treat different Central Nervous System disorders, particularly obesity, anxiety, depression, cognitive disorders, epilepsy, diabetes, arthritis, pain and other NPY5 receptor-mediated disorders in mammals, including man. The compounds object of the present invention respond to general formula (I)

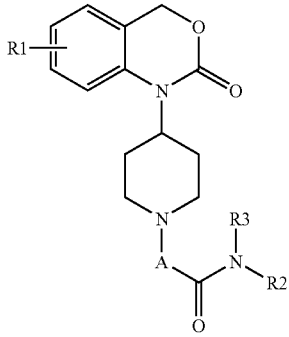

(I)

wherein $R_1$ represents hydrogen, halogen, alcoxyl or a $C_1$–$C_4$ alkyl radical;

$R_2$ represents hydrogen, a $C_1$–$C_4$ alkyl radical, a phenyl radical, a benzyl radical or, together with $R_3$ may be part of a 5 or 6-member heterocycle;

$R_3$ represents bicyclic ring, tricyclic ring, substituted phenyl or phenyl substituted by a hydrocarbonated chain which, together with $R_2$, is part of a 5 or 6-member nitrogenous heterocycle;

A represents —$CHR_4$— or —$CHR_4$—$CH_2$—

$R_4$ represents hydrogen, a $C_1$–$C_4$ alkyl radical or a phenyl radical; or one of its physiologically acceptable salts.

Preferred compounds of the invention are those wherein $R_3$ represents a phenyl substituted by a $C_1$–$C_4$ alkyl radical, methoxy, halogen, cyclohexyl, phenyl, phenoxy, phenylthio, benzoyl, phenylamino or phenyl(alkyl $C_1$–$C_4$)amino.

Other preferred compounds are those wherein $R_3$ represents a bicycle constituted by a 6-member aromatic or heteroaromatic ring and a 5 or 6-member substituted or non-substituted cycle of general formula (II)

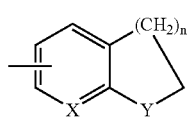

(II)

wherein

X represents CH or N;

Y represents $CH_2$, O, N—$R_5$, CH—OH or C=O;

$R_5$ represents hydrogen or a $C_1$–$C_4$ alkyl radical n represents 1 or 2.

Other preferred compounds are those wherein $R_3$ represents a tricycle constituted by a substituted or non-substituted 6-member aromatic ring, a substituted or non-substituted 5 or 6-member cycle and a substituted or non-substituted 6-member aromatic ring of general formula (III)

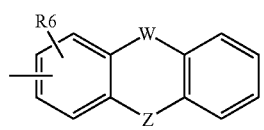

(III)

wherein

W represents a bond between the two aromatic rings, $CH_2$, CH—OH or C=O;

Z represents $CH_2$, O, CH—OH, C=O or N—$R_5$;

$R_5$ represents hydrogen or a $C_1$–$C_4$ alkyl radical;

$R_6$ represents hydrogen, alcoxyl or a $C_1$–$C_4$ alkyl radical.

The present invention also relates to the physiologically acceptable salts of the compounds of general formula (I), particularly the addition salts of mineral acids such as hydrochloric, hydrobromic, phosphoric, sulfuric, nitric acids, and of organic acids such as citric, maleic, fumaric, tartaric acids or their derivatives, p-toluensulfonic, methansulfonic, camphorsulfonic acids, etc.

The new derivatives of general formula (I), wherein $R_1$ to $R_6$, A, X, Y, W, Z and n have the above-mentioned signification, may be prepared by means of the following process, consisting in the reaction of compounds of general formula (IV):

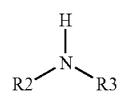

(IV)

wherein

R2 and R3 have the above-mentioned signification, with a compound of general formula (V):

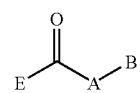

(V)

wherein

A has the above-mentioned signification, E represents a halogen, a hydroxyl or O-acyl group and wherein B represents a halogen, preferably chlorine. The reaction is performed in inert solvents and in the presence of base or/and auxiliaries, yielding compounds of general formula (VI):

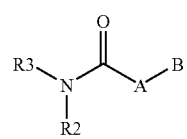

(VI)

wherein

B, A, R2 and R3 have the above-mentioned signification.

These compounds are reacted with amines of general formula (VII):

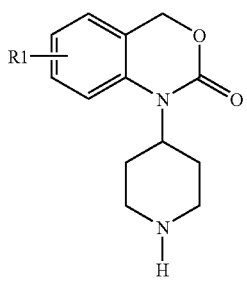

wherein

R1 has the above-mentioned signification, or with its corresponding salts, preferably hydrochloride, in inert solvents and in the presence of base and/or auxiliaries as necessary.

According to the invention, the process may be illustrated as an example by means of the following reaction outline:

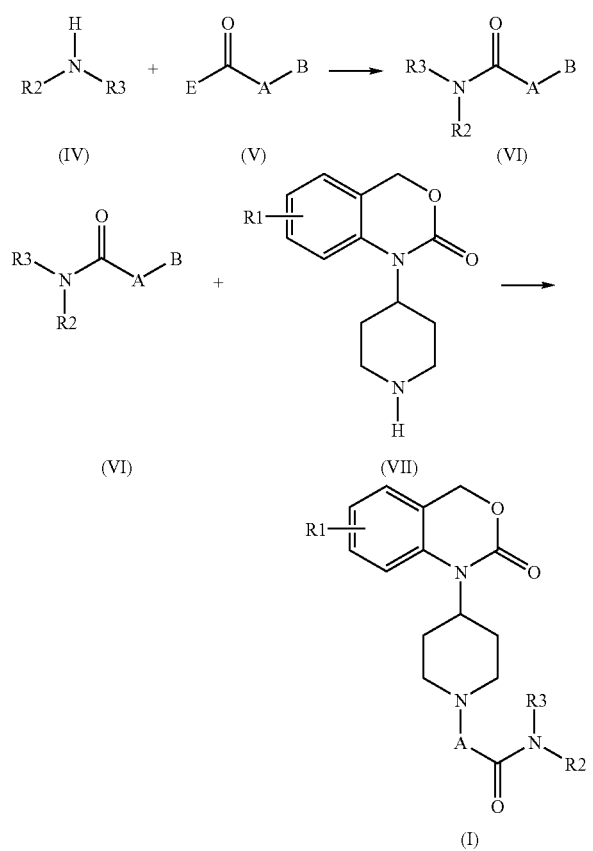

wherein $R_1$ $R_2$, $R_3$, A, B and E have the above-mentioned signification.

According to the invention, the solvents appropriate for the process are usual organic solvents, among which ethers, preferably diethyl ether, dioxane, tetrahydrofurane, dimethyl glycol ether, or alcohols, e.g. methanol, ethanol, propanol, isopropanol, butanol, isobutanol, tert-butanol, or hydrocarbons, preferably benzene, toluene, xylene, hexane, cyclohexane, petroleum ether, or halogenated hydrocarbons, e.g. dichloromethane, trichloromethane, tetrachloromethane, dichloroethylene, trichloroethylene, chlorobenzene or/and other solvents, preferably ethyl acetate, triethylamine, pyridine, dimethylsulfoxide, dimethylformamide, hexamethylphosphor-amide, acetonitrile, acetone or nitromethane, are included. Mixtures of these solvents may also be used.

According to the invention, the bases that may be used in the process are generally organic or inorganic bases, preferably alkali metal hydroxydes, e.g. sodium hydroxyde or potassium hydroxyde, or obtained from other metals such as barium hydroxyde or different carbonates, preferably potassium carbonate, sodium carbonate, calcium carbonate, or alkoxides, e.g. sodium methoxide, potassium methoxide, sodium ethoxide, potassium ethoxide or potassium tert-butoxide, or organic amines, preferably triethylamine, diisopropylethylamine or heterocycles, e.g. 1,4-diazabicyclo[2.2.2]octane, 1,8-diazabicyclo[5.4.0]undec-7-ene, pyridine, diamino pyridine, dimethylaminopyridine, methylpiperidine or morpholine. Alkali metals such as sodium or its hydrides, e.g. sodium hydride, may also be used.

The above-mentioned bases may be used for the process as auxiliaries as appropriate. Other auxiliaries may be dehydrating agents like carbodiimides, e.g. diisopropylcarbodiimide, dicyclohexylcarbodiimide, or N-(3-dimethylaminopropyl)-N'-ethylcarbodiimide hydrochloride, or carbonylic compounds, e.g. carbonyldiimidazole or compounds like isobutylchloroformate or methansulfonyl chloride, among others. These reagents are generally used in amounts ranging between 0.5 and 3 mol versus 1 mol of the corresponding carboxylic acids. In general, the bases are used in amounts ranging between 0.05 and 10 mol versus 1 mol of the invention compounds.

During some of the synthetic sequences described or while preparing the syntons used, the protection of sensitive or reactives groups in some of the molecules used may be necessary and/or desirable. This can be performed by using conventional protective groups like those described in the literature [Protective groups in Organic Chemistry, ed J. F. W. McOmie, Plenum Press, 1973; T. W. Greene & P. G. M. Wuts, Protective Groups in Organic Chemistry, John Wiley & sons, 1991]. The protective groups may be further eliminated as convenient by means of well-known methods in the art of the technique.

The invention provides pharmaceutical compositions which, in addition to a pharmaceutically acceptable excipient, comprise at least one compound of general formula (I) or one of its physiologically acceptable salts. The invention also relates to the use of a compound of general formula (I) and its physiologically acceptable salts in the manufacture of a medicinal product with NPY5 receptor antagonistic activity, useful for the prevention or treatment of several Central Nervous System disorders, particularly obesity, anxiety, depression, cognitive disorders, epilepsy, diabetes, arthritis, pain and other NPY5 receptor-mediated disorders in mammals, including man.

The methodology for the preparation of new compounds according to the invention is described below. Also disclosed is the affinity for the receptor as well as pharmaceutical formulations applicable to the compounds object of the invention. The examples below, given on a merely illustrative basis, should not in any way limit the scope of the invention.

EXAMPLE 1

Preparation of 1-{1-[N-(9-oxo-9H-fluoren-2-yl)aminocarbonylmethyl]-4-(piperidinyl)}-1,4-dihydro-2H-3,1-benzoxazin-2-one hydrochloride.

A mixture of 1-(4-piperidinyl)-1,4-dihydro-2H-3,1-benzoxazinone hydrochloride (2.68 g, 10 mmol), N-(9-oxo-9H-fluoren-2-yl)-2-chloroacetamide (2.99 g, 11 mmol) and $K_2CO_3$ (5.53 g, 40 mmol) in DMF (40 mL) was stirred overnight at room temperature. $H_2O$ (100 mL) was then added and the precipitate formed was collected by filtration. The solid was dissolved in hot ethyl acetate, washed with water, decanted, dried and evaporated to dryness. The residue dissolved in EtOH was brought to pH=3 with a 1M solution of hydrogen chloride in EtOH and filtered to yield the desired hydrochloride in crystalline form (3.73 g, 74%). Other solvents to be chosen are acetonitrile and dimethylsulfoxide.

The melting point and the spectroscopic data for the identification of some of the compounds of general formula (I) object of the present invention, prepared with the method described in Example 1, are shown in the following table:

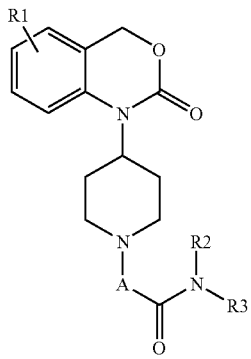

| Ex | $R_1$ | A | $R_2$ | $R_3$ | | Salt | Mp(° C.) | IR cm$^{-1}$ | $^1$H-NMR(300 MHz), δ(solvent) |
|---|---|---|---|---|---|---|---|---|---|
| 1 | H | $CH_2$ | H | | (2-fluorenone-yl) | HCl | 276–280 | 3241, 1696, 1608, 1560, 1463, 1391, 1293, 1259, 1206, 739. | 2.00(d, J=12.6 Hz, 2H), 2.90(m, J=12.6 Hz, 2H), 3.43(m, 2H), 3.66(d, J=9.7 Hz, 2H), 4.21(s, 2H), 4.28(m, 1H), 5.16(s, 2H), 7.13(m, 1H), 7.34(m, 4H), 7.59(d, J=7.0 Hz, 2H), 7.76(m, 3H), 8.00(s, 1H), 10.26(s, 1H), 11.36(s, 1H). (DMSO-$d_6$) |
| 2 | H | $CH_2$ | H | | (2-fluorenone-yl) | — | 192–194 | 1704, 1611, 1511, 1293, 1205, 768. | 1.74(d, J=10.8 Hz, 2H), 2.38(m, 2H), 2.62(m, 2H), 2.99(d, J=11.1 Hz, 2H), 3.24(s, 2H), 3.87(m, 1H), 5.12(s, 2H), 7.09(t, J=7.2 Hz, 1H), 7.27(d, J=7.7 Hz, 2H), 7.37(t, J=7.5 Hz, 2H), 7.59(m, 4H), 7.68(d, J=7.5 Hz, 1H), 8.07(s, 1H), 10.22(s, 1H). (DMSO-$d_6$) |
| 3 | H | $CH_2$ | H | | (2-fluorenone-yl) | HCl | >275 | 3433, 1705, 1609, 1557, 1467, 1451, 1297, 1253, 1111, 769 | 2.02(d, J=12.6 Hz, 2H), 2.91(m, J=12.6 Hz, 2H), 3.43(m, 2H), 3.67(d, J=9.9 Hz, 2H), 4.26(m, 3H), 5.16(s, 2H), 7.13(m, 1H), 7.30(d, J=7.5 Hz, 1H), 7.40(m, 3H), 7.64(m, 5H), 8.06(s, 1H), 10.29(s, 1H), 11.46(s, 1H). (DMSO-$d_6$) |
| 4 | H | $CH_2$ | H | | (4-benzoylphenyl) | — | 133–137 | 3630, 3449, 3249, 1682, 1600, 1516, 1498, 1316, 1282, 1045, 757, 697 | 1.73(d, J=11.7 Hz, 2H), 2.36(m, J=11.2 Hz, 2H), 2.61(m, J=11.7 Hz, 2H), 2.98(d, J=10.8 Hz, 2H), 3.22(s, 2H), 3.87(m, J=11.7 Hz, 1H), 5.11(s, 2H), 7.09(t, J=7.3 Hz, 1H), 7.27(d, J=7.3 Hz, 2H), 7.36(t, J=7.7 Hz, 1H), 7.54(t, J=7.3 Hz, 2H), 7.69(m, 5H), 7.83(s, 1H), 10.18(s, 1H). (DMSO-$d_6$) |

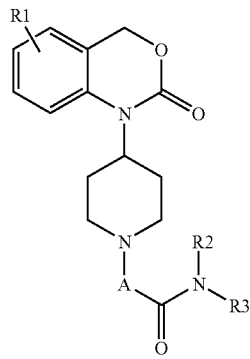

| Ex | R₁ | A | R₂ | R₃ | Salt | Mp(°C.) | IR cm⁻¹ | $^1$H-NMR(300 MHz), δ(solvent) |
|---|---|---|---|---|---|---|---|---|
| 5 | H | CH$_2$ | H | 4-benzoylphenyl | HCl | 238–243 | 3457, 1685, 1599, 1542, 1401, 1280, 1034, 700 | 2.00(d, J=11.9 Hz, 2H), 2.91(m, J=12.6 Hz, 2H), 3.41(m, 2H), 3.65(d, J=11.2 Hz, 2H), 4.26(m, 3H), 5.16(s, 2H), 7.12(m, 1H), 7.30(d, J=7.5 Hz, 1H), 7.39(d, J=3.8 Hz, 2H), 7.54(m, 2H), 7.68(m, 3H), 7.81(m, 4H), 10.31(s, 1H), 11.51(s, 1H). (DMSO-d$_6$) |
| 6 | H | CH$_2$ | H | 6-(1-oxo-tetralinyl) | HCl | 260–264 | 3400, 1710, 1671, 1592, 1549, 1391, 1260, 1204, 1043, 770 | 1.98(m, 4H), 2.52(m, 2H), 2.91(m, 4H), 3.41(m, 2H), 3.64(m, J=10.4 Hz, 2H), 4.25(m, 3H), 5.16(s, 2H), 7.14(m, 1H), 7.30(d, J=7.3 Hz, 1H), 7.40(m, 2H), 7.58(m, 2H), 7.86(d, J=8.6 Hz, 1H), 10.22(s, 1H), 11.15(s, 1H). (DMSO-d$_6$) |
| 7 | H | CH$_2$ | H | 4-(9-oxo-fluorenyl) | HCl | 270–273 | 1710, 1698, 1608, 1541, 1466, 1390, 1292, 1263, 1201, 737 | 2.03(d, J=12.1 Hz, 2H), 2.90(m, J=11.2 Hz, 2H), 3.49(m, 2H), 3.70(d, J=11.2 Hz, 2H), 4.29(m, 1H), 4.40(s, 2H), 5.16(s, 2H), 7.14(m, 1H), 7.30(d, J=7.3 Hz, 1H), 7.42(d, 4H), 7.61(m, 4H), 7.82(d, J=7.1 Hz, 1H), 10.29(s, 1H), 10.96(s, 1H). (DMSO-d$_6$) |
| 8 | H | CH$_2$ | H | 3-benzoylphenyl | HCl | 214–218 | 3447, 1686, 1609, 1592, 1298, 1208, 1043, 721 | 2.00(d, J=12.1 Hz, 2H), 2.89(m, J=11.2 Hz, 2H), 3.33(m, 2H), 3.64(d, J=10.6 Hz, 2H), 4.17(s, 2H), 4.26(m, 1H), 5.16(s, 2H), 7.13(m, 1H), 7.34(m, 3H), 7.54(m, 4H), 7.71(m, 3H), 7.86(d, J=8.1 Hz, 1H), 8.08(s, 1H), 10.17(s, 1H), 10.99(s, 1H). (DMSO-d$_6$) |
| 9 | H | CH$_2$ | H | 5-(1-oxo-indanyl) | — | 206–209 | 3327, 1720, 1696, 1592, 1514, 1285, 1206, 1045, 768, 753 | 1.73(d, J=11.5 Hz, 2H), 2.36(m, J=11.0 Hz, 2H), 2.59(m, 4H), 2.97(d, J=10.8 Hz, 2H), 3.05(m, 2H), 3.21(s, 2H), 3.86(m, 1H), 5.11(s, 2H), 7.09(t, J=7.2 Hz, 1H), 7.27(d, J=7.5 Hz, 2H), 7.36(m, 1H), 7.58(s, 2H), 7.95(s, 1H), 10.14(s, 1H). (DMSO-d$_6$) |
| 10 | H | CH$_2$ | H | 5-(1-oxo-indanyl) | HCl | 272–277 | 3463, 1709, 1595, 1555, 1390, 1284, 1256, 1204, 1042, 771 | 2.00(d, J=12.4 Hz, 2H), 2.60(m, 2H), 2.90(m, J=11.5 Hz, 2H), 3.07(m, 2H), 3.41(m, 2H), 3.63(m, 2H), 4.25(m, 3H), 5.16(s, 2H), 7.12(m, 1H), 7.30(d, J=7.1 Hz, 1H), 7.38(d, J=3.7 Hz, 2H), 7.63(s, 2H), 7.94(s, 1H), 10.28(s, 1H), 11.48(s, 1H). (DMSO-d$_6$) |

-continued

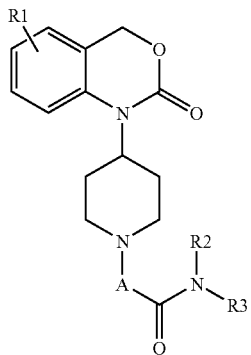

| Ex | R₁ | A | R₂ | R₃ | | Salt | Mp(° C.) | IR cm⁻¹ | ¹H-NMR(300 MHz), δ(solvent) |
|----|----|----|----|----|----|------|---------|---------|-------------------------------|
| 11 | H | CH₂ | H | (indane) | | HCl | 230–231 | 2949, 1701, 1607, 1558, 1496, 1394, 1292, 1206, 1042, 771 | 1.99(m, 4H), 2.83(m, 6H), 3.43(m, 2H), 3.63(d, J=10.1 Hz, 2H), 4.17(s, 2H), 4.29(m, 1H), 5.15(s, 2H), 7.15(m, 2H), 7.30(d, J=7.5 Hz, 1H), 7.37(m, 3H), 7.54(s, 1H), 10.24(s, 1H), 10.95(s, 1H). (DMSO-d₆) |
| 12 | H | CH₂ | H | (MeO-methyldibenzofuran) | | HCl | 182–187 | 3448, 1592, 1560, 1432, 1400, 1299, 1209, 1043, 770, 721 | 2.02(d, J=12.8 Hz, 2H), 2.91(m, J=10.6 Hz, 2H), 3.45(m, 2H), 3.68(d, J=12.1 Hz, 2H), 3.99(s, 3H), 4.29(s, 2H), 4.42(m, 1H), 5.16(s, 2H), 7.10–8.40(10H), 10.18(s, 1H), 11.18(s, 1H). (DMSO-d₆) |
| 13 | H | CH₂ | H | (4-cyclohexylphenyl) | | HCl | 256–260 | 3422, 1701, 1609, 1550, 1393, 1292, 1260, 1205, 1043 | 1.29(m, 5H), 1.72(m, 5H), 2.00(d, J=13.2 Hz, 2H), 2.45(m, 1H), 2.91(m, J=11.7 Hz, 2H), 3.39(m, 2H), 3.64(m, 2H), 4.16(s, 2H), 4.30(m, 1H), 5.15(s, 2H), 7.13(m, 3H), 7.29(d, J=7.3 Hz, 1H), 7.38(m, 2H), 7.54(d, J=8.2 Hz, 2H), 10.28(s, 1H), 10.96(s, 1H). (DMSO-d₆) |
| 14 | H | CH₂ | H | (CH₂CH₂-o-tolyl with ethyl) | | HCl | 198–203 | 3427, 1677, 1497, 1390, 1297, 1205, 1039, 753 | 1.91(m, 4H), 2.73(t, J=6.5 Hz, 2H), 2.93(m, J=11.4 Hz, 2H), 3.40(m, 2H), 3.66(m, 4H), 4.28(m, 1H), 4.52(m, 2H), 5.15(s, 2H), 7.25(m, 8H), 10.18(s, 1H). (DMSO-d₆) |
| 15 | H | CHC₆H₅ | H | (fluorenone) | | HCl | 247–249 | 3435, 1709, 1691, 1608, 1561, 1298, 766, 743 | 1.91(d, J=12.0 Hz, 1H), 2.06(d, J=12.8 Hz, 1H), 2.94(m, 3H), 3.23(m, 1H), 3.45(m, 1H), 3.78(m, 1H), 4.32(m, 1H), 5.14(s, 2H), 5.49(s, 1H), 7.12(m, 1H), 7.28(d, J=7.3 Hz, 1H), 7.38(m, 3H), 7.59(m, 8H), 7.80(m, 2H), 8.07(s, 1H), 10.73(s, 1H), 12.16(s, 1H). (DMSO-d₆) |
| 16 | H | CHCH₃ | H | (fluorenone) | | HCl | 242–252 | — | 1.62(d, J=6.4 Hz, 3H), 2.05(d, J=13.0 Hz, 2H), 2.91(m, 2H), 3.57(m, 2H), 4.35(m, 2H), 5.16(s, 2H), 7.12(m, 1H), 7.38(m, 4H), 7.65(m, 5H), 8.14(s, 1H), 10.35(s, 1H), 11.77(s, 1H). (DMSO-d₆) |
| 17 | H | CH₂ | H | (N-ethylcarbazole) | | — | 212–214 | 3298, 2975, 1713, 1684, 1531, 1492, 1208, 1040, 768, 747 | 1.29(t, J=7.0 Hz, 3H), 1.77(d, J=10.6 Hz, 2H), 2.39(m, 2H), 2.66(m, 2H), 3.04(d, J=11.6 Hz, 2H), 3.20(s, 2H), 3.90(m, 1H), 3.04(d, J=11.0 Hz, 2H), 3.20(s, 2H), 3.90(m, 1H), 4.41(q, J=7.0 Hz, 2H), 5.13(s, 2H), 7.10(t, J=7.5 Hz, 1H), 7.17(t, J=7.5 Hz, 1H), 7.29(m, 2H), 7.41(m, 2H), 7.58(m, 3H), 8.07(d, J=7.5 Hz, 1H), 8.42(s, 1H), 9.76(s, 1H). (DMSO-d₆) |

-continued

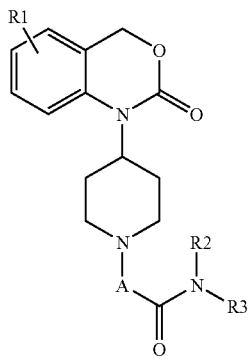

| Ex | R1 | A | R2 | R3 | Salt | Mp(° C.) | IR cm⁻¹ | $^1$H-NMR(300 MHz), δ(solvent) |
|---|---|---|---|---|---|---|---|---|
| 18 | H | CH$_2$ | H | 3-(9-ethylcarbazolyl) | HCl | 246–250 | 3248, 2966, 1683, 1608, 1493, 1299, 1226, 1040, 771, 745 | 1.28(t, J=6.8 Hz, 3H), 2.00(d, J=11.9 Hz, 3H), 2.93(m, J=11.5 Hz, 2H),3.43(m, 2H), 3.69(d, J=10.3 Hz, 2H), 4.28(m, 3H), 4.41(q, J=6.8 Hz, 2H), 5.16(s, 2H), 7.15(m, 2H), 7.30(d, J=7.3 Hz, 1H), 7.41(m, 3H), 7.62(m, 3H), 8.05(d, J=7.9 Hz, 1H), 8.47(s, 1H), 10.33(s, 1H), 11.15(s, 1H). (DMSO-d$_6$) |
| 19 | 6-CH$_3$ | CH$_2$ | H | 2-(9-fluorenonyl) | — | 237–239 | 1706, 1611, 1596, 1508, 1292, 1214 | 1.72(d, J=11.7 Hz, 2H), 2.25(s, 3H), 2.38(m, 2H), 2.62(m, 2H), 2.99(d, J=11.0 Hz, 2H), 3.23(s, 2H), 3.85(m,1H), 5.06(s, 2H), 7.06(s, 1H), 7.15(s, 2H), 7.37(t, J=7.3 Hz, 1H), 7.58(m, 4H), 7.67(d, J=7.3 Hz, 1H), 8.06(s, 1H), 10.17(s, 1H). (DMSO-d$_6$) |
| 20 | 6-CH$_3$ | CH$_2$ | H | 2-(9-fluorenonyl) | HCl | 250–252 | 3411, 1707, 1683, 1608, 1551, 1296, 1252, 1111 | 1.99(d, J=13.4 Hz, 2H), 2.27(s, 3H), 2.89(m, 2H), 3.42(m, 2H), 3.67(m, 2H), 4.28(m, 3H), 5.11(s, 2H), 7.09(m, 1H), 7.18(d, J=8.4 Hz, 1H), 7.28(d, J=8.4 Hz, 1H), 7.39(t, J=7.3 Hz, 1H), 7.61(m, 5H), 8.07(s, 1H), 10.35(s, 1H), 11.65(s, 1H). (DMSO-d$_6$) |
| 21 | 6-CH$_3$ | CH$_2$ | H | 3-(9-ethylcarbazolyl) | HCl | 247–252 | 1683, 1492, 1460, 1299, 1225 | 1.29(t, J=7.0 Hz, 3H), 2.00(d, J=11.9 Hz, 3H), 2.27(s, 3H),2.91(m, J=11.2 Hz, 2H), 3.42(m, 2H), 3.68(d, J=10.4 Hz, 2H), 4.22(m, 3H), 4.42(q, J=7.1 Hz, 2H), 5.11(s, 2H), 7.10(m, 1H), 7.18(m, 2H), 7.30(d, J=8.4 Hz, 1H), 7.45(m, 1H), 7.60(m, 3H), 8.05(d, J=7.9 Hz, 1H), 8.46(s, 1H), 10.29(s, 1H), 11.09(s, 1H). (DMSO-d$_6$) |
| 22 | 6-CH$_3$ | CH$_2$ | H | 4-cyclohexylphenyl | — | 155–157 | 2923, 2849, 1711, 1519, 1294, 1217, 1046 | 1.29(m, 5H), 1.72(m, 7H), 2.25(m, 3H), 2.36(m, 3H), 2.58(m, 2H), 2.95(d, J=10.8 Hz, 2H), 3.12(s, 2H), 3.83(m, 1H), 5.06(s, 2H), 7.06(s, 2H), 7.13(m, 4H), 7.51(d, J=8.2 Hz, 2H), 9.64(s, 1H). (DMSO-d$_6$) |
| 23 | 6-CH$_3$ | CH$_2$ | H | 4-cyclohexylphenyl | HCl | 242–246 | 3428, 2925, 1711, 1691, 1507, 1293, 1218, 1039, 827, 767 | 1.27(m, 5H), 1.71(m, 5H), 1.95(d, J=12.0 Hz, 2H), 2.26(s, 3H), 2.43(m, 1H),2.89(m, J=11.5 Hz, 2H), 3.41(m, 2H), 3.57(m, 2H), 4.17(m, 2H), 4.26(m, 1H), 5.10(s, 2H), 7.09(s, 1H), 7.17(d, J=8.6 Hz, 2H), 7.18(d, J=8.6 Hz, 1H), 7.29(d, J=8.4 Hz, 2H), 7.55(d, J=8.4 Hz, 2H), 10.32(s, 1H), 11.11(s, 1H). (DMSO-d$_6$) |

-continued

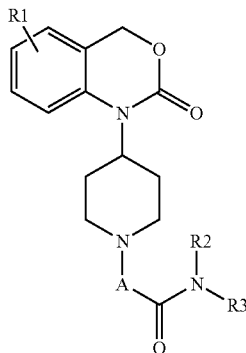

| Ex | R1 | A | R2 | R3 | Salt | Mp(° C.) | IR cm⁻¹ | ¹H-NMR(300 MHz), δ(solvent) |
|---|---|---|---|---|---|---|---|---|
| 24 | 6-CH₃ | CH₂ | H | 4-benzoylphenyl | HCl | 240–244 | 3432, 2995, 1702, 1598, 1539, 1314, 1281, 1039, 700 | 1.99(d, J=11.3 Hz, 2H), 2.27(s, 3H), 2.90(m, 2H), 3.42(m, 2H),3.65(m, 2H), 4.27(m, 3H), 5.11(s, 2H), 7.10(s, 1H), 7.18(d, J=8.2 Hz, 1H), 7.29(d, J=8.2 Hz, 2H), 7.55(t, J=7.3 Hz, 2H), 7.66(m, 3H), 7.77(d, J=8.8 Hz, 2H), 7.86(d, J=8.4 Hz, 2H), 10.35(s, 1H), 11.61(s, 1H). (DMSO-d₆) |
| 25 | H | CH₂ | H | 9-methyl-9H-carbazol-3-yl | HCl | 191–193 | 3425, 3048, 1709, 1686, 1607, 1496, 1248, 1040, 771, 750 | 2.03(d, J=12.4 Hz, 2H), 2.93(m, J=11.2 Hz, 2H), 3.42(m, 2H), 3.69(d, J=11.2 Hz, 2H),3.86(s, 3H), 4.22(s, 2H), 4.32(m, 1H), 5.17(s, 2H), 7.13(m, 1H), 7.20(d, J=7.3 Hz, 1H), 7.30(d, J=7.3 Hz, 1H), 7.43(m, 3H), 7.58(d, J=10.2 Hz, 2H), 7.65(d, J=8.6 Hz, 1H), 8.06(d, J=7.7 Hz, 1H), 8.47(s, 1H), 10.29(s, 1H), 11.09(s, 1H). (DMSO-d₆) |
| 26 | H | CH₂ | H | 3-methyl-9,10-dioxoanthracen-2-yl | HCl | 280–282 | 3466, 3078, 1679, 1591, 1551, 1332, 1293, 1201, 917, 725 | 2.03(d, J=12.1 Hz, 2H), 2.92(m, J=11.4 Hz, 2H), 3.43(m, 2H), 3.69(d, J=9.7 Hz, 2H),4.29(m, 3H), 5.16(s, 2H), 7.14(m, 1H), 7.14(m, 1H), 7.30(d, J=7.3 Hz, 1H), 7.39(d, J=7.3 Hz, 1H), 7.39(d, J=3.8 Hz, 2H), 7.92(m, 2H), 8.08(d, J=8.2 Hz, 1H), 8.21(m, 3H), 8.57(s, 1H), 10.30(s, 1H), 11.65(s, 1H). (DMSO-d₆) |
| 27 | H | CH₂ | H | 4-(N-ethyl-N-phenylamino)phenyl | HCl | 254–257 | 3432, 2980, 1714, 1689, 1508, 1492, 1258, 1204, 770, 753 | 1.09(t, J=7.0 Hz, 3H), 2.00(d, J=12.1 Hz, 2H), 2.90(m, J=11.3 Hz, 2H), 3.37(m, 2H),3.63(m, 2H), 3.71(q, J=7.0 Hz, 2H), 4.15(s, 2H), 4.29(m, 1H), 5.16(s, 2H), 6.84(m, 3H), 7.01(d, J=9.0 Hz, 2H), 7.12(m, 1H), 7.20(m, 2H), 7.30(d, J=7.3 Hz, 2H), 7.39(d, J=3.8 Hz, 2H), 7.56(d, J=8.8 Hz, 2H), 10.23(s, 1H), 10.92(s, 1H). (DMSO-d₆) |
| 28 | 6-CH₃ | CH₂ | H | 4-(N-ethyl-N-phenylamino)phenyl | HCl | 226–230 | 2976, 1708, 1690, 1509, 1378, 1291, 1256, 1216, 1040, 766 | 1.09(t, J=7.0 Hz, 3H), 1.98(d, J=13.0 Hz, 2H), 2.27(s, 3H), 2.88(m, J=11.3 Hz, 2H),3.41(m, 2H), 3.63(d, J=11.2 Hz, 2H), 3.70(q, J=7.0 Hz, 2H), 4.15(s, 2H), 4.26(m, 1H), 5.10(s, 2H), 6.84(m, 3H), 7.00(d, J=9.0 Hz, 2H), 7.10(m, 1H), 7.19(m, 2H), 7.25(m, 2H), 7.57(d, J=8.8 Hz, 2H), 10.24(s, 1H), 10.97(s, 1H). (DMSO-d₆) |

-continued

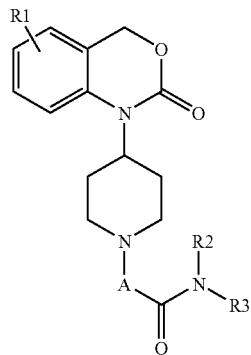

| Ex | R₁ | A | R₂ | R₃ | Salt | Mp(° C.) | IR cm⁻¹ | ¹H-NMR(300 MHz), δ(solvent) |
|---|---|---|---|---|---|---|---|---|
| 29 | H | CH₂ | H | 4-phenoxyphenyl | HCl | 242–248 | 3044, 1703, 1686, 1506, 1487, 1392, 1226, 1040, 751, 694 | 2.01(d, J=12.8 Hz, 2H), 2.90(m, J=12.1 Hz, 2H), 3.41(m, 2H), 3.63(m, 2H), 4.18(s, 2H), 4.29(m, 1H), 5.16(s, 2H), 6.96(m, 2H), 7.03(m, 2H), 7.12(m, 2H), 7.35(m, 5H), 7.67(d, J=8.8 Hz, 2H), 10.26(s, 1H), 11.13(s, 1H). (DMSO-$d_6$) |
| 30 | H | CH₂ | H | 4-(N-isopropyl-N-phenylamino)phenyl | HCl | 171–173 | 3399, 2976, 1707, 1655, 1498, 1321, 1254, 1117, 753 | 1.02(d, J=6.6 Hz, 6H), 1.92(d, J=12.4 Hz, 2H), 2.86(m, J=10.6 Hz, 2H), 3.18(m, J=11.5 Hz, 2H), 3.50(m, J=11.5 Hz, 2H), 3.65(s, 2H), 4.14(m, 1H), 4.78(hp, J =6.6 Hz, 1H), 5.14(s, 2H), 6.90(t, J=7.2 Hz, 1H), 7.12(m, 6H), 7.30(m, 6H), 8.61(s, 1H), 9.85(s, 1H). (DMSO-$d_6$) |
| 31 | H | CH₂CH₂ | H | 9-oxofluorenyl | HCl | 240–242 | — | 2.03(d, J=12.5 Hz, 2H), 2.85(m, J=12.3 Hz, 2H), 3.04(m, 2H), 3.24(m, J=12.1 Hz, 2H), 3.44(m, 2H), 3.60(m, J=11.4 Hz, 2H), 4.29(m, 1H), 5.16(s, 2H), 7.13(m, 1H), 7.30(d, J=6.8 Hz, 1H), 7.38(m, 3H), 7.62(m, 4H), 8.07(s, 1H), 10.15(s, 1H), 10.97(s, 1H). (DMSO-$d_6$) |
| 32 | 6-Cl | CH₂ | H | 9-ethylcarbazolyl | HCl | 265–268 | 2970, 1712, 1691, 1492, 1376, 1294, 1201, 1043 | 1.28(t, J=7.0 Hz, 3H), 2.01(d, J=12.4 Hz, 2H), 2.90(m, 2H), 3.43(m, 2H), 3.68(m, 2H), 4.27(m, 3H), 4.41(q, J=7.0 Hz, 2H), 5.16(s, 2H), 7.17(t, J=7.4 Hz, 1H), 7.44(m, 4H), 7.61(m, 3H), 8.05(d, J=7.9 Hz, 1H), 8.47(s, 1H), 10.33(s, 1H), 11.16(s, 1H). (DMSO-$d_6$) |
| 33 | H | CH₂ | H | 4-chlorophenyl | HCl | 272–276 | 3454, 3057, 1701, 1610, 1552, 1492, 1394, 1292, 1254, 1024 | 1.99(d, J=12.4 Hz, 2H), 2.90(m, J=11.5 Hz, 2H), 3.40(m, 2H), 3.63(d, J=11.0 Hz, 2H), 4.20(s, 2H), 4.28(m, 1H), 5.15(s, 2H), 7.12(m, 1H), 7.29(d, J=7.3 Hz, 1H), 7.40(m, 4H), 7.69(d, J=8.8 Hz, 2H), 10.28(s, 1H), 11.35(s, 1H). (DMSO-$d_6$) |
| 34 | 6-Cl | CH₂ | H | 4-chlorophenyl | HCl | 279–282 | 3026, 1713, 1698, 1612, 1553, 1491, 1294, 1253, 1199, 1042 | 1.99(d, J=12.7 Hz, 2H), 2.86(m, 2H), 3.41(m, 2H), 3.62(d, J=10.4 Hz, 2H), 4.18(s, 2H), 4.27(m, 2H), 5.16(s, 2H), 7.40(m, 5H), 7.68(d, J=8.8 Hz, 2H), 10.26(s, 1H), 11.24(s, 1H). (DMSO-$d_6$) |
| 35 | 8-CH₃ | CH₂ | H | 9-oxofluorenyl | HCl | 233–236 | 3410, 3014, 1701, 1609, 1561, 1450, 1371, 1285, 1237, 1109, 916, 768, 731 | 2.13(d, J=12.8 Hz, 2H), 2.40(s, 3H), 2.91(m, 2H), 3.42(m, 2H), 3.63(d, J=10.2 Hz, 2H), 3.84(m, 1H), 4.25(s, 2H), 5.09(s, 2H), 7.10(m, 2H), 7.25(d, J=6.8 Hz, 1H), 7.38(t, J=7.4 Hz, 1H), 7.62(m, 5H), 8.07(s, 1H), 10.27(s, 1H), 11.75(s, 1H). (DMSO-$d_6$) |

-continued

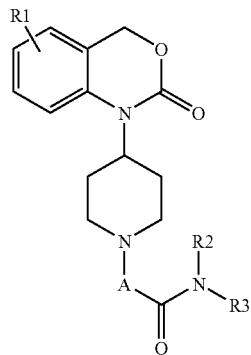

| Ex | R₁ | A | R₂ | R₃ | Salt | Mp(° C.) | IR cm⁻¹ | ¹H-NMR(300 MHz), δ(solvent) |
|---|---|---|---|---|---|---|---|---|
| 36 | 6-Cl | CH₂ | H | (2-fluorenone-yl) | HCl | 245–249 | 3421, 1701, 1609, 1560, 1371, 1298, 1201 | 2.01(d, J=11.8 Hz, 2H), 2.88(m, 2H), 3.42(m, 2H), 3.66(d, J=11.8 Hz, 2H), 4.30(m, 3H), 5.16(s, 2H), 7.39(m, 4H), 7.60(m, 5H), 8.08(s, 1H), 10.39(s, 1H), 11.75(s, 1H). (DMSO-d₆) |
| 37 | 8-CH₃ | CH₂ | H | (9-hydroxyfluorenyl) | HCl | 207–212 | 3435, 1679, 1390, 1263, 774 | 2.13(d, J=13.3 Hz, 2H), 2.40(s, 3H), 2.91(m, J=12.0 Hz, 2H), 3.36(m, 2H), 3.63(d, J=10.8 Hz, 2H), 3.83(m, 1H), 4.18(s, 2H), 5.09(s, 2H), 5.45(s, 1H), 5.86(broad, 1H), 7.11(m, 2H), 7.33(m, 3H), 7.55(m, 3H), 7.64(d, J=7.3 Hz, 1H), 8.05(s, 1H), 10.19(s, 1H), 11.22(s, 1H). (DMSO-d₆) |
| 38 | H | CH₂ | H | (9-hydroxyfluorenyl) | HCl | >225(dec.) | 3406, 3059, 1702, 1604, 1461, 1395, 1205, 1042, 769, 739 | 2.01(d, J=12.8 Hz, 2H), 2.91(m, 2H), 3.42(m, 2H), 3.66(d, J=9.6 Hz, 2H), 4.22(s, 2H), 4.29(m, 1H), 5.16(s, 2H), 5.45(s, 1H), 5.92(broad, 1H), 7.12(m, 1H), 7.32(m, 5H), 7.55(d, J=7.2 Hz, 1H), 7.62(d, J=8.1 Hz, 1H), 7.72(m, 2H), 7.96(s, 1H), 10.27(s, 1H), 11.17(s, 1H). (DMSO-d₆) |
| 39 | 6-Cl | CH₂ | H | (9-hydroxyfluorenyl) | HCl | 219–222 | 3422, 3045, 1701, 1559, 1491, 1295, 1200, 1042 | 2.01(d, J=11.9 Hz, 2H), 2.88(m, 2H), 3.39(m, 2H), 3.66(d, J=9.8 Hz, 2H), 4.27(m, 3H), 5.16(s, 2H), 5.45(s, 1H), 5.86(broad, 1H), 7.36(m, 5H), 7.54(m, 3H), 7.64(d, J=7.2 Hz, 1H), 8.06(s, 1H), 10.28(s, 1H), 11.17(s, 1H). (DMSO-d₆) |
| 40 | 8-CH₃ | CH₂ | H | (9-ethylcarbazolyl) | HCl | 229–232 | 3449, 2976, 1710, 1685, 1490, 1384, 1326, 1225, 953, 745 | 1.28(t, J=7.0 Hz, 3H), 2.13(d, J=12.8 Hz, 2H), 2.40(s, 3H), 2.92(m, 2H), 3.40(m, 2H), 3.64(d, J=11.0 Hz, 2H), 3.84(m, 1H), 4.17(s, 2H), 4.41(q, J=7.0 Hz, 2H), 5.09(s, 2H), 7.13(m, 3H), 7.25(d, J=7.3 Hz, 1H), 7.44(m, 1H), 7.60(m, 3H), 8.05(d, J=7.7 Hz, 1H), 8.43(s, 1H), 10.18(s, 1H), 11.09(s, 1H). (DMSO-d₆) |
| 41 | 8-CH₃ | CH₂ | H | (4-CF₃-phenyl) | HCl | 264–274 | 3449, 2990, 1703, 1610, 1556, 1327, 1119, 1065, 952, 844 | 2.1(d, J=12.7 Hz, 2H) 2.4(s, 3H) 2.9(m, 2H) 3.4(m, 2H) 3.6(d, J=12.0 Hz, 2H) 3.8(t, J=11.5 Hz, 1H) 4.1(s, 2H) 5.1(s, 2H) 7.1(m, 2H) 7.2(d, J=7.1 Hz, 1H) 7.7(d, J=8.5 Hz, 2H) 7.8(s, 2H) 10.2(s, 1H) 11.1(s, 1H). (DMSO-d6) |
| 42 | 8-CH₃ | CH₂ | H | phenyl | HCl | 232–239 | 3190, 1696, 1599, 1556, 951, 773, 726, 694 | 2.1(d, J=13.7 Hz, 2H) 2.4(s, 3H) 3.0(m, 2H) 3.2(s, 2H) 3.6(m, 2H) 3.8(m, 1H) 4.1(s, 2H) 5.0(s, 2H) 7.1(m, 3H) 7.2(d, J=7.8 Hz, 1H) 7.3(t, J=6.5 Hz, 2H) 7.6(d, J=8.1 Hz, 2H) 10.1(s, 1H) 10.6(s, 1H). (DMSO-d6) |

-continued

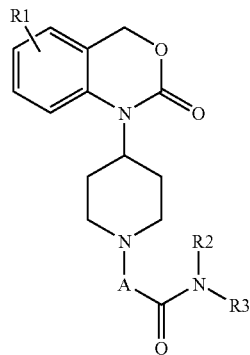

| Ex | R$_1$ | A | R$_2$ | R$_3$ | Salt | Mp(° C.) | IR cm$^{-1}$ | $^1$H-NMR(300 MHz), δ(solvent) |
|---|---|---|---|---|---|---|---|---|
| 43 | H | CH$_2$ | H | 4-CF$_3$-C$_6$H$_4$ | HCl | 276–284 | 3407, 3055, 1708, 1610, 1555, 1324, 1112, 1065, 948, 845 | 2.0(d, J=13.9 Hz, 2H) 2.9(q, J=12.0 Hz, 2H) 3.3(m, 2H) 3.6(d, J=12.2 Hz, 2H) 4.2(s, 2H) 4.3(d, J=12.2 Hz, 1H) 5.1(s, 2H) 7.1(m, 1H) 7.2(d, J=7.3 Hz, 1H) 7.3(d, J=3.7 Hz, 2H) 7.6(d, J=8.8 Hz, 2H) 7.8(m, 2H) 10.2(s, 1H) 10.9(s, 1H). (DMSO-d6) |
| 44 | 6-Cl | CH$_2$ | H | C$_6$H$_5$ | HCl | 265–277 | 3001, 2494, 1712, 1696, 1602, 1559, 1259, 1041, 966, 760 | 2.0(d, J=13.9 Hz, 2H) 2.9(m, 2H) 3.3(m, 2H) 3.6(d, J=12.2 Hz, 2H) 4.1(s, 2H) 4.3(m, 1H) 5.1(s, 2H) 7.1(t, J=7.3 Hz, 1H) 7.3(m, 2H) 7.4(m, 3H) 7.6(d, J=7.6 Hz, 2H) 10.1(s, 1H) 10.6(s, 1H). (DMSO-d6) |
| 45 | 6-Cl | CH$_2$ | H | 4-CF$_3$-C$_6$H$_4$ | HCl | 284–285 | 2993, 2500, 1707, 1611, 1557, 1325, 1112, 1064, 949, 845 | 2.0(d, J=12.9 Hz, 2H) 2.9(q, J=13.2 Hz, 2H) 3.3(m, 2H) 3.6(d, J=12.0 Hz, 2H) 4.2(s, 2H) 4.3(m, 1H) 5.1(s, 2H) 7.4(m, 3H) 7.7(m, 2H) 7.8(m, 2H) 10.2(s, 1H) 11.0(s, 1H). (DMSO-d6) |
| 46 | H | CH$_2$ | H | C$_6$H$_5$ | HCl | 262–272 | 3405, 3068, 1707, 1609, 1557, 1259, 1043, 947, 761 | 2.0(d, J=13.4 Hz, 2H) 2.9(m, 2H) 3.3(m, 2H) 3.6(d, J=11.7 Hz, 2H) 4.1(s, 2H) 4.3(m, 1H) 5.1(s, 2H) 7.1(dd, J=7.3, 5.9 Hz, 2H) 7.3(m, 5H) 7.6(d, J=8.5 Hz, 2H) 10.1(s, 1H) 10.6(s, 1H). (DMSO-d6) |
| 47 | 8-CH$_3$ | CH$_2$ | H | 4-Cl-C$_6$H$_4$ | HCl | 245–253 | 3277, 2991, 1726, 1681, 1597, 1541, 1492, 1280, 1255, 1201 | 2.1(d, J=13.2 Hz, 2H) 2.4(s, 3H) 2.9(m, 2H) 3.3(m, 2H) 3.6(d, J=2.9 Hz, 2H) 3.8(m, 1H) 4.1(s, 2H) 5.0(s, 2H) 7.1(m, 2H) 7.2(d, J=7.1 Hz, 1H) 7.3(d, J=7.1 Hz, 2H) 7.6(m, 2H) 10.2(s, 1H) 10.8(s, 1H). (DMSO-d6) |
| 48 | H | CH$_2$ | H | 4-CN-C$_6$H$_4$ | HCl | 268–282 | 3401, 2992, 2217, 1708, 1600, 1538, 1391, 1042, 950, 842 | 2.0(d, J=12.7 Hz, 2H) 2.9(m, 2H) 3.4(m, 2H) 3.7(d, J=11.5 Hz, 2H) 4.3(m, 3H) 5.1(s, 2H) 7.1(m, 1H) 7.3(d, J=7.8 Hz, 1H) 7.4(m, 2H) 7.8(m, 4H) 10.2(s, 1H) 11.1(s, 1H). (DMSO-d6) |
| 49 | 8-CH$_3$ | CH$_2$ | H | 4-CN-C$_6$H$_4$ | HCl | 229–234 | 3448, 2978, 2223, 1707, 1600, 1541, 1035, 950, 839 | 2.1(d, J=13.4 Hz, 2H) 2.4(s, 3H) 2.9(m, 2H) 3.3(m, 2H) 3.6(d, J=11.4 Hz, 2H) 3.8(t, J=11.0 Hz, 1H) 4.1(s, 2H) 5.1(s, 2H) 7.1(m, 2H) 7.2(d, J=6.4 Hz, 1H) 7.7(m, 4H) 10.2(s, 1H) 11.1(s, 1H). (DMSO-d6) |
| 50 | 6-Cl | CH$_2$ | H | 4-CN-C$_6$H$_4$ | HCl | 274–278 | 3414, 2986, 2219, 1721, 1602, 1541, 1313, 1200, 1040, 842 | 2.0(d, J=12.6 Hz, 2H) 2.9(m, 2H) 3.3(m, 2H) 3.6(d, J=12.2 Hz, 2H) 4.2(s, 2H) 4.3(m, 1H) 5.1(s, 2H) 7.4(m, 3H) 7.8(s, 4H) 10.2(s, 1H) 11.0(s, 1H). (DMSO-d6) |

-continued

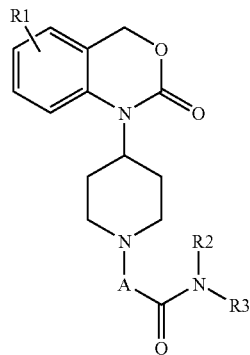

| Ex | R₁ | A | R₂ | R₃ | Salt | Mp(° C.) | IR cm⁻¹ | ¹H-NMR(300 MHz), δ(solvent) |
|---|---|---|---|---|---|---|---|---|
| 51 | H | CH₂ | H | 4-acetylphenyl | HCl | >280 | 3448, 3044, 1708, 1600, 1395, 1261, 1043, 948, 842, 771 | 2.0(d, J=13.5 Hz, 2H) 2.5(s, 3H) 2.9(m, 2H) 3.3(m, 2H) 3.6(d, J=11.4 Hz, 2H) 4.1(s, 2H) 4.3(m, 1H) 5.1(s, 2H) 7.1(m, 1H) 7.2(d, J=7.3 Hz, 1H) 7.3(m, 2H) 7.7(d, J=8.8 Hz, 2H) 7.9(d, J=8.8 Hz, 2H) 10.2(s,1H) 10.8(s, 1H). (DMSO-d6) |
| 52 | 8-CH₃ | CH₂ | H | 4-phenoxyphenyl | HCl | 162–167 | 3414, 3039, 1710, 1691, 1506, 1487, 1228 | 2.1(d, J=13.0 Hz, 2H) 2.3(s, 3H) 2.9(q, J=11.9 Hz, 2H) 3.2(m, 2H) 3.6(d, J=11.1 Hz, 2H) 3.8(t, J=11.3 Hz, 1H) 4.0(s, 2H) 5.0(s, 2H) 6.9(m, 4H) 7.0(m, 3H) 7.2(d, J=7.0 Hz, 1H) 7.3(t, J=8.4 Hz, 2H) 7.6(d, J=8.9 Hz, 2H) 10.1(s, 1H) 10.6(s, 1H). (DMSO-d6) |
| 53 | 6-Cl | CH₂ | H | 4-acetylphenyl | HCl | 244–286 | 3579, 3475, 2992, 1717, 1667, 1600, 1545, 1263, 1041, 948 | 2.0(d, J=13.7 Hz, 2H) 2.5(s, 3H) 2.9(m, 2H) 3.4(m, 2H) 3.7(d, J=11.9 Hz, 2H) 4.2(s, 2H) 4.3(m, 1H) 5.1(s, 2H) 7.4(m, 3H) 7.7(d, J=8.6 Hz, 2H) 8.0(d, J=8.6 Hz, 2H) 10.2(s, 1H) 11.0(s, 1H). (DMSO-d6) |
| 54 | 8-CH₃ | CH₂ | H | 4-acetylphenyl | HCl | >280 | 3422, 2967, 1701, 1676, 1590, 1407, 1256, 950, 835, 773 | 2.1(d, J=14.5 Hz, 2H) 2.4(s, 3H) 2.5(s, 3H) 2.9(m, 2H) 3.3(t, J=13.5 Hz, 2H) 3.6(d, J=12.3 Hz, 2H) 3.8(t, J=11.4 Hz, 1H) 4.1(s, 2H) 5.1(s, 2H) 7.1(m, 2H) 7.2(d, J=7.3 Hz, 1H) 7.7(d, J=8.8 Hz, 2H) 7.9(d, J=8.8 Hz, 2H) 10.2(s, 1H) 10.9(s, 1H). (DMSO-d6) |
| 55 | 6-Cl | CH₂ | H | 4-phenoxyphenyl | HCl | 262–267 | 2990, 1714, 1560, 1488, 1231, 1039, 950, 871, 751 | 2.0(d, J=13.2 Hz, 2H) 2.9(m, 2H) 3.3(m, 2H) 3.6(d, 2H) 4.1(s, 2H) 4.3(m, 1H) 5.1(s, 2H) 7.0(m, 4H) 7.1(t, J=7.4 Hz, 1H) 7.3(m, 5H) 7.6(d, J=9.0 Hz, 2H) 10.2(s, 1H) 10.6(s, 1H). (DMSO-d6) |
| 56 | 8-CH₃ | CH₂ | H | 4-benzoylphenyl | HCl | 217 | 3432, 2894, 1701, 1649, 1597, 1541, 1281, 1033, 925, 857 | 2.1(d, J=13.4 Hz, 2H) 2.4(s, 3H) 2.9(m, 2H) 3.3(m, 2H) 3.6(d, J=11.4 Hz, 2H) 3.8(m, 1H) 4.1(s, 2H) 5.0(s, 2H) 7.1(m, 2H) 7.2(d, J=7.5 Hz, 1H) 7.5(m, 2H) 7.6(dd, J=6.9, 2.1 Hz, 1H) 7.7(dd, J=8.2, 1.3 Hz, 2H) 7.8(s, 4H) 10.2(s, 1H) 10.9(s, 1H). (DMSO-d6) |
| 57 | 6-Cl | CH₂ | H | 4-benzoylphenyl | HCl | 256–259 | 3449, 3051, 1708, 1599, 1541, 1315, 1203, 1041, 949, 702 | 2.0(d, J=13.2 Hz, 2H) 2.9(m, 2H) 3.3(m, 2H) 3.6(d, J=9.9 Hz, 2H) 4.2(s, 2H) 4.2(m, 1H) 5.1(s, 2H) 7.3(m, 3H) 7.5(t, J=7.3 Hz, 2H) 7.6(t, J=7.9 Hz, 1H) 7.7(m, 2H) 7.7(m, 4H) 10.2(s, 1H) 10.9(s, 1H). (DMSO-d6) |

-continued

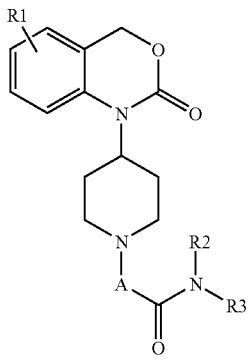

| Ex | R1 | A | R2 | R3 | Salt | Mp(° C.) | IR cm⁻¹ | ¹H-NMR(300 MHz), δ(solvent) |
|---|---|---|---|---|---|---|---|---|
| 58 | 6-CH$_3$ | CH$_2$ | H | 2-Cl-phenyl | — | 146–148 | 3177, 3045, 1701, 1595, 1492, 1215, 1046, 966, 808 | 1.9(d, J=13.7 Hz, 2H) 2.3(s, 3H) 2.4(m, 2H) 2.9(m, J=12.4, 4.0 Hz, 2H) 3.1(m, 2H) 3.2(s, 2H) 3.8(m, 1H) 5.1(s, 2H) 6.9(m, 2H) 7.1(d, J=8.4 Hz, 1H) 7.3(d, J=8.8 Hz, 2H) 7.6(d, J=8.8 Hz, 2H) 9.2(s, 1H). (CDCl$_3$-d) |
| 59 | 6-CH$_3$ | CH$_2$ | H | 2-CF$_3$-phenyl | — | 169–173 | 3302, 3068, 1730, 1706, 1609, 1508, 1329, 1114, 1067, 846 | 1.9(d, J=11.7 Hz, 2H) 2.3(s, 3H) 2.4(m, 2H) 2.9(qd, J=12.6, 4.1 Hz, 2H) 3.1(d, J=11.5 Hz, 2H) 3.2(s, 2H) 3.8(t, J=12.0 Hz, 1H) 5.1(s, 2H) 6.9(m, 2H) 7.1(d, J=9.0 Hz, 1H) 7.6(d, J=8.8 Hz, 2H) 7.8(d, J=9.0 Hz, 2H) 9.4(s, 1H). (CDCl$_3$-d) |
| 60 | 6-CH$_3$ | CH$_2$ | H | phenyl | — | 154–157 | 3550, 2799, 1697, 1601, 1522, 1443, 1213, 1047, 817, 764 | 1.9(d, J=11.7 Hz, 2H) 2.3(s, 3H) 2.4(t, J=11.2 Hz, 2H) 2.9(qd, J=12.4, 3.6 Hz, 2H) 3.1(d, J=11.7 Hz, 2H) 3.2(s, 2H) 3.8(tt, J=12.0, 3.7 Hz, 1H) 5.1(s, 2H) 6.9(d, J=8.4 Hz, 1H) 7.1(m, 2H) 7.4(m, 2H) 7.6(d, J=7.6 Hz, 2H) 9.2(s, 1H). (CDCl$_3$-d) |
| 61 | 8-CH$_3$ | CH$_2$ | H | 4-cyclohexylphenyl | HCl | 249–253 | 3449, 2922, 2849, 1695, 1611, 1550, 1257, 1037, 952, 832 | 1.3(m, 4H) 1.7(m, 6H) 2.1(d, J=12.1 Hz, 2H) 2.3(s, 3H) 2.4(s, 1H) 2.9(m, 2H) 3.2(t, J=11.6 Hz, 2H) 3.6(d, J=10.8 Hz, 2H) 3.8(t, J=10.6 Hz, 1H) 4.0(s, 2H) 5.0(s, 2H) 7.0(m, 2H) 7.1(m, 3H) 7.4(d, J=8.4 Hz, 2H) 10.0(br, 1H) 10.4(s, 1H). (DMSO-d6) |
| 62 | 6-Cl | CH$_2$ | H | 4-cyclohexylphenyl | HCl | 249–256 | 2929, 1692, 1607, 1547, 1293, 1201, 1043, 830 | 1.3(m, 4H) 1.7(m, 6H) 2.0(d, J=15.7 Hz, 2H) 2.4(m, 1H) 2.9(q, J=12.5 Hz, 2H) 3.3(t, J=11.9 Hz, 2H) 3.6(d, J=10.3 Hz, 2H) 4.1(s, 2H) 4.2(t, J=12.1 Hz, 1H) 5.1(s, 2H) 7.1(d, J=8.6 Hz, 2H) 7.4(m, 3H) 7.5(d, J=8.6 Hz, 2H) 10.1(br, 1H) 10.5(s, 1H). (DMSO-d6) |
| 63 | H | CH$_2$ | H | 2-benzoylphenyl | HCl | 211–216 | 3260, 3058, 1681, 1610, 1296, 1036, 954, 772 | 1.9(d, J=13.7 Hz, 2H) 2.8(m, 2H) 3.1(m, 2H) 3.3(d, J=10.6 Hz, 2H) 3.9(s, 2H) 4.2(t, J=10.3 Hz, 1H) 5.1(s, 2H) 7.1(t, J=7.1 Hz, 1H) 7.4(m, 8H) 7.6(m, 2H) 7.7(d, J=7.1 Hz, 2H) 10.1(br, 1H) 10.8(s, 1H). (DMSO-d6) |

-continued

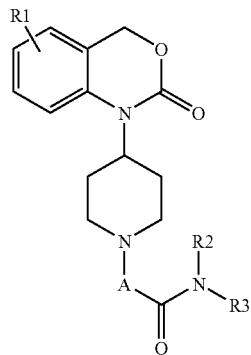

| Ex | R₁ | A | R₂ | R₃ | Salt | Mp(° C.) | IR cm⁻¹ | ¹H-NMR(300 MHz), δ(solvent) |
|---|---|---|---|---|---|---|---|---|
| 64 | 8-CH₃ | CH₂ | H | 2-methylbenzoylphenyl | HCl | 168–176 | 3413, 2961, 1686, 1606, 1282, 1033, 951, 775 | 2.0(d, J=13.4 Hz, 2H) 2.3(s, 3H) 2.8(m, 2H) 3.0(m, 2H) 3.3(d, J=10.8 Hz, 2H) 3.7(t, J=12.2 Hz, 1H) 3.8(s, 2H) 5.0(s, 2H) 7.0(d, 2H) 7.2(d, J=7.7 Hz, 1H) 7.3(t, J=7.5 Hz, 1H) 7.4(m, 4H) 7.6(m, 2H) 7.7(d, J=7.7 Hz, 2H) 10.0(s, 1H) 10.7(s, 1H). (DMSO-d6) |
| 65 | 6-Cl | CH₂ | H | 2-methylbenzoylphenyl | HCl | 167–178 | 3259, 1686, 1491, 1299, 1205, 1041, 956, 770 | 1.9(d, J=12.8 Hz, 2H) 2.7(m, 2H) 3.1(m, 2H) 3.3(d, J=10.6 Hz, 2H) 3.9(s, 2H) 4.2(m, 1H) 5.1(s, 2H) 7.4(m, 5H) 7.5(m, 3H) 7.6(m, 2H) 7.7(d, J=8.1 Hz, 2H) 10.0(s, 1H) 10.8(s, 1H). (DMSO-d6) |
| 66 | 6-CH₃ | CH₂ | H | 2-methylbenzoylphenyl | — | 167–170 | 3448, 2938, 1702, 1634, 1509, 1445, 1156, 1045 | 1.8(d, J=9.3 Hz, 2H) 2.3(s, 3H) 2.5(m, 2H) 2.9(qd, J=12.6, 3.5 Hz, 2H) 3.0(d, J=11.2 Hz, 2H) 3.2(s, 2H) 4.3(tt, J=12.8, 4.6 Hz, 1H) 5.0(s, 2H) 7.0(m, 2H) 7.1(m, 1H) 7.5(m, 2H) 7.6(m, 4H) 7.8(m, 2H) 8.7(d, J=8.1 Hz, 1H) 11.9(s, 1H). (CDCl₃-d) |
| 67 | 6-CH₃ | CH₂ | H | 4-methyl-phenoxyphenyl | HCl | 234–237 | 3148, 2970, 2449, 1691, 1541, 1507, 1233, 1038 | 2.0(d, J=14.1 Hz, 2H) 2.2(s, 3H) 2.9(m, 2H) 3.3(m, 2H) 3.6(d, J=12.1 Hz, 2H) 4.1(s, 2H) 4.2(m, 1H) 5.1(s, 2H) 7.0(m, 6H) 7.2(m, 2H) 7.3(t, J=7.8 Hz, 2H) 7.6(d, J=9.0 Hz, 2H) 10.1(s, 1H) 10.6(s, 1H). (DMSO-d6) |
| 68 | 6-CH₃ | CH₂ | H | 4-methyl-acetylphenyl | HCl | 273–277 | 2927, 1705, 1666, 1594, 1595, 1508, 1267, 1117, 946, 839 | 2.0(d, J=13.2 Hz, 2H) 2.2(s, 3H) 2.5(s, 3H) 2.9(m, 2H) 3.4(m, 2H) 3.6(d, J=12.1 Hz, 2H) 4.2(m, 3H) 5.1(s, 2H) 7.1(s, 1H) 7.2(m, 2H) 7.7(d, J=8.8 Hz, 2H) 7.9(d, J=8.8 Hz, 2H) 10.2(br, 1H) 10.9(s, 1H). (DMSO-d6) |
| 69 | H | CH₂ | H | 3-methyl-9-hydroxyfluorenyl | HCl | 270–273 | 3328, 3071, 2547, 1715, 1691, 1606, 1259, 1045, 775 | 2.0(d, J=11.5 Hz, 2H) 2.9(m, 2H) 3.4(m, 2H) 3.7(d, J=12.3 Hz, 2H) 4.2(s, 2H) 4.3(m, 1H) 5.1(s, 2H) 5.4(s, 1H) 7.1(m, 2H) 7.3(m, 2H) 7.3(m, 3H) 7.5(dd, J=8.2, 1.8 Hz, 1H) 7.6(m, 2H) 7.6(d, J=7.1 Hz, 1H) 8.0(d, J=1.6 Hz, 1H) 10.1(s, 1H) 10.7(s, 1H). (DMSO-d6) |

-continued

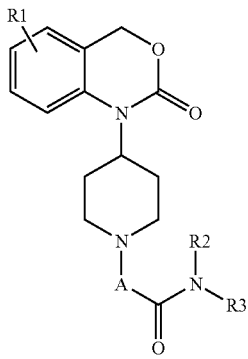

| Ex | R₁ | A | R₂ | R₃ | Salt | Mp(° C.) | IR cm⁻¹ | ¹H-NMR(300 MHz), δ(solvent) |
|---|---|---|---|---|---|---|---|---|
| 70 | 6-Cl | CH₂ | H | 2-methyl-9H-fluoren-9-one | HCl | >300(dec) | 2999, 1707, 1603, 1561, 1490, 1463, 1298, 1200 | 2.0(d, J=11.7 Hz, 2H) 2.8(m, 2H) 3.1(m, 2H) 3.5(d, 2H) 4.3(m, 3H) 5.2(s, 2H) 7.3(m, 1H) 7.4(m, 3H) 7.6(m, 2H) 7.7(m, 3H) 8.0(s, 1H) 10.3(s, 1H) 11.4(s, 1H). (DMSO-d6) |
| 71 | 6-CH₃ | CH₂ | H | 2-methyl-9H-fluoren-9-one | HCl | 281–285 | 2985, 1701, 1604, 1561, 1466, 1300, 1262 | 2.0(d, J=11.7 Hz, 2H) 2.3(s, 3H) 2.9(m, 2H) 3.2(m, 2H) 3.6(d, 2H) 4.2(m, 3H) 5.1(s, 2H) 7.1(s, 1H) 7.3(m, 3H) 7.6(m, 2H) 7.7(m, 3H) 8.0(s, 1H) 10.3(s, 1H) 11.4(s, 1H). (DMSO-d6) |
| 72 | 8-CH₃ | CH₂ | H | 2-methyl-9H-fluoren-9-one | HCl | >300(dec) | 3448, 1686, 1603, 1561, 1463, 1304, 1276 | 2.0(d, J=11.9 Hz, 2H) 2.4(s, 3H) 2.9(m, 2H) 3.3(m, 2H) 3.6(d, 2H) 3.8(m, 1H) 4.2(s, 2H) 5.1(s, 2H) 7.1(m, 2H) 7.3(m, 3H) 7.6(m, 2H) 7.7(m, 3H) 8.0(s, 1H) 10.3(s, 1H) 11.4(s, 1H). (DMSO-d6) |
| 73 | 6-Cl | CH₂ | H | 2-methyl-9H-fluoren-9-ol | HCl | 286–289 | 3423, 3000, 1707, 1603, 1560, 1491, 1460, 1201, 1041 | 2.0(d, J=12.3 Hz, 2H) 2.9(m, 2H) 3.3(m, 2H) 3.7(d, J=11.2 Hz, 2H) 4.1(s, 2H) 4.3(m, 1H) 5.1(s, 2H) 5.4(s, 1H) 7.2(t, J=7.3 Hz, 1H) 7.3(t, J=7.4 Hz, 1H) 7.4(m, 3H) 7.5(m, 2H) 7.7(t, J=8.8 Hz, 2H) 7.9(s, 1H) 10.2(s, 1H) 10.7(s, 1H). (DMSO-d6) |
| 74 | 6-CH₃ | CH₂ | H | 2-methyl-9H-fluoren-9-ol | HCl | 196–199 | 3392, 3045, 1695, 1560, 1458, 1295, 1217, 1040 | 2.0(d, J=12.1 Hz, 2H) 2.3(s, 3H) 2.9(m, 2H) 3.4(m, 2H) 3.7(d, J=11.4 Hz, 2H) 4.3(m, 3H) 5.1(s, 2H) 5.5(s, 1H) 5.9(br, 1H) 7.1(s, 1H) 7.2(d, J=8.4 Hz, 1H) 7.3(m, 2H) 7.3(t, J=7.0 Hz, 1H) 7.6(d, J=7.1 Hz, 1H) 7.6(d, J=7.9 Hz, 1H) 7.7(m, 2H) 8.0(s, 1H) 10.3(s, 1H) 11.2(s, 1H). (DMSO-d6) |
| 75 | 8-CH₃ | CH₂ | H | 2-methyl-9H-fluoren-9-ol | HCl | 283–285 | 3260, 1688, 1618, 1563, 1467, 1384, 1309, 1280 | 2.1(d, J=13.5 Hz, 2H) 2.4(s, 3H) 2.9(m, 2H) 3.3(m, 2H) 3.6(d, J=11.0 Hz, 2H) 3.8(t, J=11.7 Hz, 1H) 4.1(s, 2H) 5.1(s, 2H) 5.4(s, 1H) 7.1(m, 2H) 7.2(td, J=7.4, 1.2 Hz, 2H) 7.3(m, 1H) 7.5(d, J=6.8 Hz, 2H) 7.7(m, 2H) 7.9(d, J=1.5 Hz, 1H) 10.1(s, 1H) 10.7(s, 1H). (DMSO-d6) |
| 76 | 6-CH₃ | CH₂ | H | 3-methyl-9H-fluoren-9-ol | HCl | 238–241 | 3399, 1693, 1618, 1559, 1295, 1217, 1041 | 2.0(d, J=13.2 Hz, 2H) 2.2(s, 3H) 2.9(m, 2H) 3.3(m, 2H) 3.7(d, J=11.0 Hz, 2H) 4.1(s, 2H) 4.2(m, 1H) 5.0(s, 1H) 5.4(s, 1H) 7.0(s, 1H) 7.1(d, J=8.4 Hz, 1H) 7.3(m, 3H) 7.4(d, J=8.2 Hz, 1H) 7.5(m, 2H) 7.6(d, J=7.3 Hz, 1H) 8.0(s, 1H) 10.1(s, 1H) 10.7(s, 1H). (DMSO-d6) |

-continued

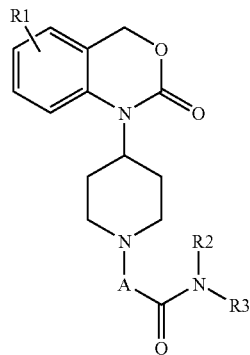

| Ex | R₁ | A | R₂ | R₃ | Salt | Mp(° C.) | IR cm⁻¹ | $^1$H-NMR(300 MHz), δ(solvent) |
|---|---|---|---|---|---|---|---|---|
| 77 | 7-F | CH₂ | H | 4-cyclohexylphenyl | HCl | 273 | 2922, 1719, 1691, 1609, 1512, 1387, 1200, 1042, 830 | 1.2(m, 1H) 1.4(m, 4H) 1.7(d, J=11.1 Hz, 1H)1.8(m, 4H) 2.0(d, J=11.6 Hz, 2H) 2.5(m, 1H) 2.9(d, J=10.6 Hz, 2H) 3.4(m, 2H) 3.6(m, 2H) 4.2(s, 2H) 4.3(m, 1H) 5.2(s, 2H) 7.0(t, J=8.3 Hz, 1H) 7.2(d, J=8.1 Hz, 2H) 7.4(m, 2H) 7.5(d, J=8.1 Hz, 2H) 10.2(s, 1H) 10.9(s, 1H). (DMSO-d6) |
| 78 | 5-F | CH₂ | H | 9-ethylcarbazol-3-yl | HCl | 266 | 1717, 1693, 1625, 1479, 1306, 1242, 1207, 1067, 781, 749 | 1.3(t, J=7.1 Hz, 3H) 2.1(d, J=12.1 Hz, 2H) 2.9(d, J=10.1 Hz, 2H)3.4(m, 2H) 3.7(m, 2H) 4.2(s, 2H) 4.4(m, 1H) 4.4(q, J=7.1 Hz, 2H) 5.3(s, 2H) 7.1(t, J=8.6 Hz, 1H) 7.2(t, J=7.3 Hz, 1H) 7.3(d, J=8.1 Hz, 1H) 7.5(m, 2H) 7.6(m, 3H) 8.1(d, J=7.6 Hz, 1H) 8.5(s, 1H) 10.3(s, 1H) 11.0(s, 1H). (DMSO-d6) |
| 79 | 6-OCH₃ | CH₂ | H | 9-ethylcarbazol-3-yl | HCl | 258 | 2944, 1673, 1503, 1491, 1283, 1229, 1036, 809, 739 | 1.3(t, J=7.1 Hz, 3H) 2.0(d, J=11.6 Hz, 2H) 2.9(d, J=10.6 Hz, 2H) 3.4(m, 2H) 3.7(m, 2H) 3.8(s, 3H)4.2(s, 2H) 4.3(m, 1H) 4.4(q, J=6.9 Hz, 2H) 5.1(s, 2H) 6.9(m, 2H) 7.2(t, J=7.7 Hz, 1H) 7.4(d, J=8.6 Hz, 1H) 7.5(t, J=7.6 Hz, 1H) 7.6(m, 3H) 8.1(d, J=7.6 Hz, 1H) 8.5(s, 1H) 10.3(s, 1H) 11.0(s, 1H). (DMSO-d6) |
| 80 | 7-CH₃ | CH₂ | H | 9-ethylcarbazol-3-yl | HCl | 263 | 2973, 1712, 1491, 1385, 1299, 1227, 1037, 806, 737 | 1.3(t, J=6.8 Hz, 3H) 2.0(d, J=12.6 Hz, 2H) 2.4(s, 3H) 3.0(d, J=14.1 Hz, 2H) 3.5(m, 2H) 3.7(m, 2H) 4.2(s, 2H) 4.3(m, 1H) 4.4(q, J=6.9 Hz, 2H) 5.1(s, 2H) 7.0(d, J=8.1 Hz, 1H) 7.2(m, 3H) 7.5(t, J=7.6 Hz, 1H) 7.6(m, 3H) 8.1(d, J=8.1 Hz, 1H) 8.5(s, 1H) 10.3(s, 1H) 11.0(s, 1H). (DMSO-d6) |
| 81 | 5-Cl | CH₂ | H | 9-ethylcarbazol-3-yl | HCl | 234 | 1692, 1589, 1462, 1301, 1229, 1047, 783 | 1.3(t, J=6.8 Hz, 3H) 2.1(d, J=11.1 Hz, 2H) 2.9(m, 2H) 3.4(m, 2H) 3.7(d, J=11.6 Hz, 2H) 4.2(s, 2H) 4.3(m, 1H) 4.4(q, J=6.6 Hz, 2H) 5.3(s, 2H) 7.2(t, J=7.3 Hz, 1H) 7.3(d, J=7.1 Hz, 1H) 7.5(m, 3H) 7.6(m, 3H) 8.1(d, J=7.6 Hz, 1H) 8.5(s, 1H) 10.2(s, 1H) 10.9(s, 1H). (DMSO-d6) |
| 82 | 5-F | CH₂ | H | 4-phenoxyphenyl | HCl | 237 | 2989, 1719, 1624, 1507, 1488, 1229, 1071, 779 | 2.0(d, J=12.6 Hz, 2H) 2.9(d, J=11.1 Hz, 2H) 3.4(m, 2H) 3.6(m, 2H) 4.2(s, 2H) 4.3(t, J=11.6 Hz, 1H) 5.3(s, 2H) 7.0(d, J=8.1 Hz, 2H) 7.0(m, 3H) 7.1(t, J=7.3 Hz, 1H) 7.3(d, J=8.6 Hz, 1H) 7.4(t, J=8.1 Hz, 2H) 7.5(m, 1H) 7.7(d, J=9.1 Hz, 2H) 10.3(s, 1H) 11.1(s, 1H). (DMSO-d6) |

-continued

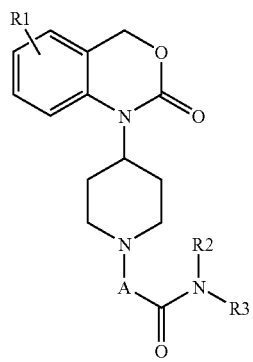

| Ex | R₁ | A | R₂ | R₃ | | Salt | Mp(° C.) | IR cm⁻¹ | ¹H-NMR(300 MHz), δ(solvent) |
|---|---|---|---|---|---|---|---|---|---|
| 83 | 6-OCH₃ | CH₂ | H | fluorenone | | — | 223 | 3293, 1701, 1507, 1465, 1294, 1218, 1040 | 1.9(d, J=12.1 Hz, 2H) 2.5(t, J=11.6 Hz, 2H) 2.9(m, 2H) 3.1(d, J=11.6 Hz, 2H) 3.2(s, 2H) 3.8(s, 4H) 5.1(s, 2H) 6.7(d, J=2.0 Hz, 1H) 6.9(m, 1H) 7.0(m, 1H) 7.3(t, J=7.6 Hz, 1H) 7.4(d, J=8.1 Hz, 1H) 7.5(t, J=7.6 Hz, 1H) 7.6(m, 3H) 8.0(s, 1H) 9.5(s, 1H). (CDCl₃-d) |
| 84 | 8-OCH₃ | CH₂ | H | dibenzofuran | | — | 88 | 1718, 1483, 1286, 1223, 1191, 1079, 1037 | 2.0(d, J=11.6 Hz, 2H) 2.4(t, J=10.9 Hz, 2H) 2.9(qd, J=12.3, 4.0 Hz, 2H) 3.1(d, J=11.6 Hz, 2H)3.2(s, 2H) 3.8(m, 1H) 3.9(s, 3H) 5.0(s, 2H) 6.8(d, J=7.1 Hz, 1H) 6.9(d, J=7.6 Hz, 1H) 7.1(m, 1H) 7.3(t, J=7.6 Hz, 1H) 7.5(t, J=7.8 Hz, 1H) 7.6(m, 3H) 8.0(d, J=7.1 Hz, 1H) 8.4(d, J=2.0 Hz, 1H) 9.4(s, 1H). (CDCl₃-d) |
| 85 | 7-Cl | CH₂ | H | dibenzofuran | | — | 237 | 3270, 1719, 1676, 1604, 1508, 1483, 1195, 1048, 749 | 1.9(d, J=12.1 Hz, 2H) 2.5(t, J=11.1 Hz, 2H) 2.9(qd, J=12.5, 4.0 Hz, 2H) 3.1(d, J=11.6 Hz, 2H) 3.2(s, 2H) 3.8(m, 1H) 5.1(s, 2H) 7.1(s, 1H) 7.1(s, 2H) 7.3(t, J=7.1 Hz, 1H) 7.5(t, J=7.8 Hz, 1H) 7.6(m, 3H) 8.0(d, J=7.1 Hz, 1H) 8.4(d, J=2.0 Hz, 1H) 9.3(s, 1H). (CDCl₃-d) |
| 86 | 6-F | CH₂ | H | fluorenone | | — | 237 | 3270, 1706, 1509, 1271, 1206, 1109, 1042, 764 | 1.9(d, J=12.1 Hz, 2H) 2.5(t, J=11.6 Hz, 2H) 2.9(m, 2H)3.1(d, J=11.6 Hz, 2H) 3.2(s, 2H) 3.8(t, J=11.9 Hz, 1H) 5.1(s, 2H) 6.9(d, J=6.6 Hz, 1H) 7.0(m, 1H) 7.1(t, J=7.1 Hz, 1H) 7.3(t, J=7.3 Hz, 1H) 7.4(d, J=7.6 Hz, 1H) 7.5(t, J=7.3 Hz, 1H) 7.6(d, J=7.6 Hz, 1H) 7.6(m, 2H) 8.0(s, 1H) 9.4(s, 1H). (CDCl₃-d) |
| 87 | 7-F | CH₂ | H | fluorenol | | — | 136 | 3399, 1719, 1618, 1509, 1199, 1042, 769 | 1.9(d, J=12.1 Hz, 2H) 2.4(t, J=11.9 Hz, 2H) 2.9(m, 2H) 3.2(s, 2H) 3.8(qd, J=12.1, 3.8 Hz, 1H) 5.1(s, 2H) 5.6(s, 1H) 6.8(m, 2H) 7.1(m, 1H) 7.3(t, J=6.8 Hz, 1H) 7.4(m, 2H) 7.6(m, 3H) 8.0(d, J=2.0 Hz, 1H) 9.2(s, 1H). (CDCl₃-d) |
| 88 | 5-CH₃ | CH₂ | H | carbazole | | — | 213 | 3247, 1701, 1476, 1245, 1204, 1033, 730 | 1.9(d, J=11.6 Hz, 2H) 2.3(s, 3H) 2.4(t, J=11.4 Hz, 2H) 2.9(qd, J=12.3,4.0 Hz, 2H) 3.1(d, J=11.6 Hz, 2H) 3.2(s, 2H) 3.8(ddd, J=11.9, 8.1, 3.8 Hz, 1H) 5.1(s, 2H) 6.9(d, J=7.8 Hz, 2H) 7.2(m, 3H) 7.4(m, 3H) 7.5(dd, J=8.6, 2.0 Hz, 1H) 8.1(d, J=7.6 Hz, 1H) 8.3(s, 1H) 8.4(s, 1H) 9.2(s, 1H). (CDCl₃-d) |

-continued

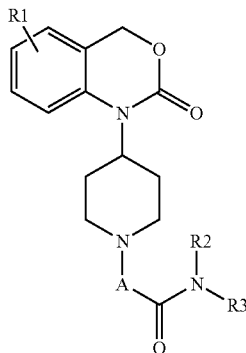

| Ex | R₁ | A | R₂ | R₃ | Salt | Mp(° C.) | IR cm⁻¹ | ¹H-NMR(300 MHz), δ(solvent) |
|---|---|---|---|---|---|---|---|---|
| 89 | 5-F | CH₂ | H | carbazol-3-yl (NH) | — | 195 | 3278, 1718, 1654, 1624, 1479, 1242, 1204, 1067, 772 | 1.9(d, J=13.6 Hz, 2H) 2.4(m, 2H) 2.9(qd, J=12.3, 3.5 Hz, 2H) 3.2(d, J=11.6 Hz, 2H) 3.2(s, 2H) 3.9(m, 1H) 5.2(s, 2H) 6.9(d, J=9.1 Hz, 2H) 7.2(ddd, J=8.0, 5.2, 3.0 Hz, 1H) 7.3(m, 1H) 7.4(m, 3H) 7.5(dd, J=8.8, 2.3 Hz, 1H) 8.1(d, J=7.6 Hz, 1H) 8.1(s, 1H) 8.4(s, 1H) 9.2(s, 1H). (CDCl₃-d) |
| 90 | 6-OCH₃ | CH₂ | H | carbazol-3-yl (NH) | — | 135 | 3293, 1701, 1502, 1289, 1215, 1042, 802, 746, 726 | 1.9(d, J=10.6 Hz, 2H) 2.4(t, J=11.1 Hz, 2H) 2.9(qd, J=12.5, 3.5 Hz, 2H) 3.1(d, J=11.6 Hz, 2H)3.2(s, 2H) 3.8(s, 3H) 3.8(m, 1H) 5.1(s, 2H) 6.7(d, J=2.5 Hz, 1H) 6.9(m, 1H) 7.0(d, J=9.1 Hz, 1H) 7.2(ddd, J=7.8, 5.6, 2.3 Hz, 1H) 7.4(m, 3H) 7.5(dd, J=8.6, 2.0 Hz, 1H) 8.1(d, J=8.1 Hz, 1H) 8.3(s, 1H) 8.4(d, J=2.0 Hz, 1H) 9.2(s, 1H). (CDCl₃-d) |
| 91 | 5-OCH₃ | CH₂ | H | 9-ethyl-carbazol-3-yl | — | 100 | 2920, 1719, 1676, 1604, 1478, 1257, 1086, 772, 749 | 1.4(t, J=7.1 Hz, 3H) 1.9(d, J=12.1 Hz, 2H) 2.4(t, J=11.4 Hz, 2H)2.9(m, 2H) 3.2(d, J=11.6 Hz, 2H) 3.2(s, 2H) 3.9(m, 4H) 4.4(q, J=7.1 Hz, 2H) 5.2(s, 2H) 6.7(d, J=8.6 Hz, 1H) 6.7(d, J=8.1 Hz, 1H) 7.2(t, J=7.3 Hz, 1H) 7.3(t, J=8.3 Hz, 1H) 7.4(m, 2H) 7.5(m, 1H) 7.6(dd, J=8.6, 2.0 Hz, 1H) 8.1(d, J=8.1 Hz, 1H) 8.4(d, J=2.0 Hz, 1H) 9.2(s, 1H). (CDCl₃-d) |
| 92 | 5-OCH₃ | CH₂ | H | 4-phenoxyphenyl | — | 73 | 2943, 1719, 1605, 1509, 1478, 1257, 1082, 772 | 1.9(d, J=11.6 Hz, 2H) 2.4(m, 2H) 2.9(m, 2H) 3.1(d, J=11.1 Hz, 2H) 3.2(m, 2H) 3.8(m, 1H) 3.9(m, 3H) 5.2(m, 2H) 6.7(m, 2H) 7.0(m, 4H) 7.1(m, 1H) 7.3(m, 3H) 7.6(m, 2H) 9.1(s, 1H). (CDCl₃-d) |
| 93 | 7-CH₃ | CH₂ | H | 9-hydroxy-fluoren-2-yl | — | 136 | 3406, 2935, 1686, 1500, 1459, 1289, 1215, 1043 | 1.9(d, J=11.1 Hz, 2H) 2.4(m, 2H) 2.9(qd, J=12.4, 3.8 Hz, 2H) 3.1(d, J=11.6 Hz, 2H) 3.2(s, 2H) 3.8(m, 4H) 5.1(s, 2H) 5.3(s, 1H) 6.7(d, J=2.5 Hz, 1H) 6.9(m, 1H) 7.0(d, J=8.6 Hz, 1H) 7.2(m, 1H) 7.4(m, 3H) 7.5(dd, J=8.6, 2.0 Hz, 1H) 8.1(d, J=7.6 Hz, 1H) 8.3(s, 1H) 8.4(d, J=2.0 Hz, 1H) 9.2(s, 1H). (CDCl₃-d) |
| 94 | 8-OCH₃ | CH₂ | H | 9-hydroxy-fluoren-2-yl | — | 143 | 3422, 1701, 1522, 1491, 1286, 1225, 1036, 768, 737 | 2.0(d, J=9.6 Hz, 2H) 2.3(t, J=11.9 Hz, 2H) 2.8(m, 2H) 3.1(d, J=11.1 Hz, 2H) 3.1(s, 2H) 3.8(m, 1H) 3.9(s, 3H) 5.0(s, 2H) 5.6(s, 1H) 6.8(d, J=7.1 Hz, 1H) 6.9(d, J=8.1 Hz, 1H) 7.1(t, J=7.8 Hz, 1H) 7.4(m, 2H) 7.5(dd, 8.1, 2.0 Hz, 1H) 7.6(m, 2H) 7.7(d, J=7.6 Hz, 1H) 8.0(s, 1H) 9.3(s, 1H). (CDCl₃-d) |

-continued

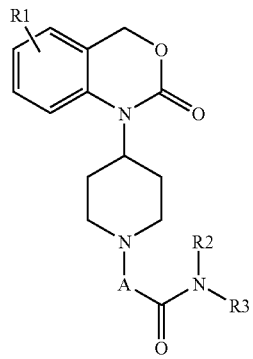

| Ex | R₁ | A | R₂ | R₃ | Salt | Mp(° C.) | IR cm⁻¹ | ¹H-NMR(300 MHz), δ(solvent) |
|---|---|---|---|---|---|---|---|---|
| 95 | 5-CH₃ | CH₂ | H | (2-methyldibenzofuran-yl) | — | 204 | 3330, 1719, 1685, 1526, 1482, 1193, 1041, 773 | 1.9(d, J=12.1 Hz, 2H) 2.3(s, 3H) 2.4(m, 2H) 3.0(qd, J=12.5, 3.5 Hz, 2H) 3.1(d, J=11.6 Hz, 2H) 3.2(s, 2H) 3.8(qd, J=12.1, 3.8 Hz, 1H) 5.1(s, 2H) 6.9(m, 2H) 7.3(m, 1H) 7.3(t, J=7.1 Hz, 1H) 7.5(t, J=7.8 Hz, 1H) 7.6(m, 3H) 8.0(d, J=7.6 Hz, 1H) 8.4(d, J=2.0 Hz, 1H) 9.3(s, 1H). (CDCl₃-d) |
| 96 | 7-CH₃ | CH₂ | H | N-ethyl-N-phenyl-(4-methylphenyl) | — | 199 | 1718, 1686, 1520, 1492, 1383, 1309, 1247, 1210, 1044 | 1.2(t, J=7.1 Hz, 3H) 1.9(d, J=10.6 Hz, 2H) 2.4(m, 5H) 2.9(qd, J=12.5, 4.0 Hz, 2H) 3.1(d, J=11.6 Hz, 2H) 3.2(s, 2H) 3.8(q, J=7.1 Hz, 2H) 3.8(m, 1H) 5.1(s, 2H) 6.9(m, 5H) 7.0(m, 3H) 7.2(m, 2H) 7.5(d, J=8.6 Hz, 2H) 9.1(s, 1H). (CDCl₃-d) |
| 97 | 8-Cl | CH₂ | H | (3-methylcarbazol-yl) | — | 180 | 3289, 1735, 1663, 1527, 1494, 1460, 1225, 1183, 1041 | 2.1(s, 2H) 2.4(t, J=10.9 Hz, 2H) 2.9(qd, J=12.4, 3.8 Hz, 2H) 3.1(d, J=11.6 Hz, 2H) 3.2(s, 2H) 3.9(tq, J=11.7, 3.8 Hz, 1H) 5.0(s, 2H) 7.1(m, 2H) 7.2(m, 1H) 7.4(m, 4H) 7.6(dd, J=8.6, 2.0 Hz, 1H) 8.1(s, 1H) 8.1(d, J=7.6 Hz, 1H) 8.4(d, J=2.0 Hz, 1H) 9.3(s, 1H). (CDCl₃-d) |
| 98 | 8-OCH₃ | CH₂ | H | N-ethyl-N-phenyl-(4-methylphenyl) | — | 216 | 3422, 2980, 1701, 1510, 1492, 1388, 1287, 1252, 1088, 1029 | 1.2(t, J=7.1 Hz, 3H) 2.2(d, J=12.1 Hz, 2H) 2.9(m, 2H) 3.3(m, 2H) 3.7(d, J=11.1 Hz, 2H) 3.8(q, J=7.1 Hz, 2H) 4.0(s, 3H) 4.1(m, 1H) 4.2(s, 2H) 5.2(s, 2H) 6.9(m, 4H) 7.1(d, J=8.6 Hz, 2H) 7.2(m, 2H) 7.3(m, 2H) 7.6(d, J=8.6 Hz, 2H) 10.2(s, 1H) 11.0(s, 1H). (CDCl₃-d) |
| 99 | H | CH₂ | H | (9-hydroxy-4-methylfluoren-yl) | — | 209–210 | 3356, 1715, 1686, 1608, 1498, 1467, 1389, 1291, 1204, 1043, 738 | 2.0(d, J=9.7 Hz, 2H) 2.5(t, J=12.3 Hz, 2H) 3.0(m, 2H) 3.2(d, J=11.0 Hz, 2H) 3.3(s, 2H) 3.9(m, 1H) 5.1(s, 2H) 5.6(d, J=9.7 Hz, 1H) 7.1(m, 2H) 7.2(d, J=8.1 Hz, 1H) 7.4(m, 4H) 7.7(d, J=7.3 Hz, 1H) 7.8(t, J=7.8 Hz, 1H) 8.0(d, J=7.3 Hz, 1H) 8.3(d, J=8.4 Hz, 1H) 9.7(s, 1H) |
| 100 | H | CH₂ | H | (α-hydroxy-4-methylbenzhydryl) | — | 240–249 | 3292, 3041, 2638, 1700, 1397, 1204, 1041, 745 | 2.0(d, J=13.4 Hz, 2H) 2.9(m, 2H) 3.4(m, 2H) 3.6(d, J=11.2 Hz, 2H) 4.1(s, 2H) 4.3(m, 1H) 5.1(s, 2H) 5.7(s, 1H) 7.1(m, 1H) 7.2(m, 2H) 7.3(m, 4H) 7.3(m, 4H) 7.5(m, 1H) 7.6(m, 1H) 10.1(s, 1H) 10.6(s, 1H) |

The compounds prepared according to example 1, corresponding to the general formula I, are the following:

[1] 1-{1[N-(9-oxo-9H-fluoren-2-yl)aminocarbonylmethyl]-4-(piperidinyl)}-1,4-dihydro-2H-3,1-benzoxazin-2-one hydrochloride, alternatively nomenclated as:
2-[4-(2-oxo-4H-benzo[d][1,3]oxazin-1-yl)-piperidin-1-yl]-N-(9-oxo-9H-fluoren-2-yl)-acetamide

[2] 1-{1-[N-(9-oxo-9H-fluoren-3-yl)aminocarbonylmethyl]-4-(piperidinyl)}-1,4-dihydro-2H-3,1-benzoxazin-2-one, alternatively nomenclated as:
2-[4-(2-oxo-4H-benzo[d][1,3]oxazin-1-yl)-piperidin-1-yl]-N-(9-oxo-9H-fluoren-3-yl)-acetamide

[3] 1-{1-[N-(9-oxo-9H-fluoren-3-yl)aminocarbonylmethyl]-4-(piperidinyl)}-1,4-dihydro-2H-3,1-benzoxazin-2-one hydrochloride, alternatively nomenclated as:
2-[4-(2-oxo-4H-benzo[d][1,3]oxazin-1-yl)-piperidin-1-yl]-N-(9-oxo-9H-fluoren-3-yl)-acetamide hydrochloride

[4] 1-{1-[N-(4-benzoylphenyl)aminocarbonylmethyl]-4-(piperidinyl)}-1,4-dihydro-2H-3,1-benzoxazin-2-one, alternatively nomenclated as:
N-(4-benzoyl-phenyl)-2-[4-(2-oxo-4H-benzo[d][1,3]oxazin-1-yl)-piperidin-1-yl]-acetamide

[5] 1-{1-[N-(4-benzoylphenyl)aminocarbonylmethyl]-4-(piperidinyl)}-1,4-dihydro-2H-3,1-benzoxazin-2-one hydrochloride, alternatively nomenclated as:
N-(4-benzoyl-phenyl)-2-[4-(2-oxo-4H-benzo[d][1,3]oxazin-1-yl)-piperidin-1-yl]-acetamide hydrochloride

[6] 1-{1-[N-(1-oxo-1,2,3,4-tetrahydronaphthalen-6-yl)aminocarbonylmethyl]-4-(piperidinyl)}-1,4-dihydro-2H-3,1-benzoxazin-2-one hydrochloride, alternatively nomenclated as:
2-[4-(2-oxo-4H-benzo[d][1,3]oxazin-1-yl)-piperidin-1-yl]-N-(5-oxo-5,6,7,8-tetrahydro-naphthalen-2-yl)-acetamide hydrochloride

[7] 1-{1-[N-(9-oxo-9H-fluoren-4-yl)aminocarbonylmethyl]-4-(piperidinyl)}-1,4-dihydro-2H-3,1-benzoxazin-2-one hydrochloride, alternatively nomenclated as:
2-[4-(2-oxo-4H-benzo[d][1,3]oxazin-1-yl)-piperidin-1-yl]-N-(9-oxo-9H-fluoren-4-yl)-acetamide hydrochloride

[8] 1-{1-[N-(3-benzoylphenyl)aminocarbonylmethyl]-4-(piperidinyl)}-1,4-dihydro-2H-3,1-benzoxazin-2-one hydrochloride, alternatively nomenclated as:
N-(3-benzoyl-phenyl)-2-[4-(2-oxo-4H-benzo[d][1,3]oxazin-1-yl)-piperidin-1-yl]-acetamide hydrochloride

[9] 1-{1-[N-(1-oxoindan-5-yl)aminocarbonylmethyl]-4-(piperidinyl)}-1,4-dihydro-2H-3,1-benzoxazin-2-one, alternatively nomenclated as:
2-[4-(2-oxo-4H-benzo[d][1,3]oxazin-1-yl)-piperidin-1-yl]-N-(1-oxo-indan-5-yl)-acetamide

[10] 1-{1-[N-(1-oxoindan-5-yl)aminocarbonylmethyl]-4-(piperidinyl)}-1,4-dihydro-2H-3,1-benzoxazin-2-one hydrochloride, alternatively nomenclated as:
2-[4-(2-oxo-4H-benzo[d][1,3]oxazin-1-yl)-piperidin-1-yl]-N-(1-oxo-indan-5-yl)-acetamide hydrochloride

[11] 1-{1-[N-(5-indanyl)aminocarbonylmethyl]-4-(piperidinyl)}-1,4-dihydro-2H-3,1-benzoxazin-2-one hydrochloride, alternatively nomenclated as:
N-Indan-5-yl-2-[4-(2-oxo-4H-benzo[d][1,3]oxazin-1-yl)-piperidin-1-yl]-acetamide hydrochloride

[12] 1-{1-[N-(2-methoxydibenzofuran-3-yl)aminocarbonylmethyl]-4-(piperidinyl)}-1,4-dihydro-2H-3,1-benzoxazin-2-one hydrochloride, alternatively nomenclated as:
N-(2-Methoxy-dibenzofuran-3-yl)-2-[4-(2-oxo-4H-benzo[d][1,3]oxazin-1-yl)-piperidin-1-yl]-acetamide hydrochloride

[13] 1-{1-[N-(4-cyclohexylphenyl)aminocarbonylmethyl]-4-(piperidinyl)}-1,4-dihydro-2H-3,1-benzoxazin-2-one hydrochloride, alternatively nomenclated as:
N-(4-Cyclohexyl-phenyl)-2-[4-(2-oxo-4H-benzo[d][1,3]oxazin-1-yl)-piperidin-1-yl]-acetamide hydrochloride

[14] 1-{1-[((1-quinolinyl)carbonylmethyl-4-(piperidinyl)}-1,4-dihydro-2H-3,1-benzoxazin-2-one hydrochloride, alternatively nomenclated as:
1-{1-[2-(3,4-Dihydro-2H-quinolin-1-yl)-2-oxo-ethyl]piperidin-4-yl}-1,4-dihydro-benzo[d][1,3]oxazin-2-one hydrochloride

[15] 1-{1-[1-phenyl-N-(9-oxo-9H-fluoren-3-yl)aminocarbonylmethyl]-4-(piperidinyl)}-1,4-dihydro-2H-3,1-benzoxazin-2-one hydrochloride, alternatively nomenclated as:
2-[4-(2-oxo-4H-benzo[d][1,3]oxazin-1-yl)-piperidin-1-yl]-N-(9-oxo-9H-fluoren-3-yl)-2-phenyl-acetamide hydrochloride

[16] 1-{1-[N-(9-oxo-9H-fluoren-3-yl)aminocarbonyleth-1-yl]-4-(piperidinyl)}-1,4-dihydro-2H-3,1-benzoxazin-2-one hydrochloride, alternatively nomenclated as:
2-[4-(2-oxo-4H-benzo[d][1,3]oxazin-1-yl)-piperidin-1-yl]-N-(9-oxo-9H-fluoren-3-yl)-propionamide hydrochloride

[17] 1-{1-[N-(9-ethyl-9H-carbazol-3-yl)aminocarbonylmethyl]-4-(piperidinyl)}-1,4-dihydro-2H-3,1-benzoxazin-2-one, alternatively nomenclated as:
N-(9-Ethyl-9H-carbazol-3-yl)-2-[4-(2-oxo-4H-benzo[d][1,3]oxazin-1-yl)-piperidin-1-yl]-acetamide

[18] 1-{1-[N-(9-ethyl-9H-carbazol-3-yl)aminocarbonylmethyl]-4-(piperidinyl)}-1,4-dihydro-2H-3,1-benzoxazin-2-one hydrochloride, alternatively nomenclated as:
N-(9-Ethyl-9H-carbazol-3-yl)-2-[4-(2-oxo-4H-benzo[d][1,3]oxazin-1-yl)-piperidin-1-yl]-acetamide hydrochloride

[19] 1-{1-[N-(9-oxo-9H-fluoren-3-yl)aminocarbonylmethyl]-4-(piperidinyl)}-6-methyl-1,4-dihydro-2H-3,1-benzoxazin-2-one, alternatively nomenclated as:
2-[4-(6-methyl-2-oxo-4H-benzo[d][1,3]oxazin-1-yl)-piperidin-1-yl]-N-(9-oxo-9H-fluoren-3-yl)-acetamide

[20] 1-{1-[N-(9-oxo-9H-fluoren-3-yl)aminocarbonylmethyl]-4-(piperidinyl)}-6-methyl-1,4-dihydro-2 H-3,1-benzoxazin-2-one hydrochloride, alternatively nomenclated as:
2-[4-(6-methyl-2-oxo-4H-benzo[d][1,3]oxazin-1-yl)-piperidin-1-yl]-N-(9-oxo-9H-fluoren-3-yl)-acetamide hydrochloride

[21] 1-{1-[N-(9-ethyl-9H-carbazol-3-yl)aminocarbonylmethyl]-4-(piperidinyl)}-6-methyl-1,4-dihydro-2H-3,1-benzoxazin-2-one hydrochloride, alternatively nomenclated as:
N-(9-Ethyl-9H-carbazol-3-yl)-2-[4-(6-methyl-2-oxo-4H-benzo[d][1,3]oxazin-1-yl)-piperidin-1-yl]-acetamide hydrochloride

[22] 1-{1-[N-(4-cyclohexylphenyl)aminocarbonylmethyl]-4-(piperidinyl)-6-methyl-1,4-dihydro-2H-3,1-benzoxazin-2-one, alternatively nomenclated as:
N-(4-cyclohexyl-phenyl)-2-[4-(6-methyl-2-oxo-4H-benzo[d][1,3]oxazin-1-yl)-piperidin-1-yl]-acetamide

[23] 1-{1-[N-(4-cyclohexylphenyl)aminocarbonylmethyl]-4-(piperidinyl)-}6-methyl-1,4-dihydro-2H-3,1-benzoxazin-2-one hydrochloride, alternatively nomenclated as:
N-(4-Cyclohexyl-phenyl)-2-[4-(6-methyl-2-oxo-4H-benzo[d][1,3]oxazin-1-yl)-Piperidin-1-yl]-acetamide hydrochloride

[24] 1-{1-[N-(4-benzoylphenyl)aminocarbonylmethyl]-4-(piperidinyl)}-6-methyl-1,4-dihydro-2H-3,1-benzoxazin-2-one hydrochloride, alternatively nomenclated as:

N-(4-benzoyl-phenyl)-2-[4-(6-methyl-2-oxo-4H-benzo[d][1,3]oxazin-1-yl)-piperidin-1-yl]-acetamide hydrochloride

[25] 1-{1-[N-(9-methyl-9H-carbazol-3-yl)aminocarbonylmethyl]-4-(piperidinyl)}-1,4-dihydro-2H-3,1-benzoxazin-2-one hydrochloride, alternatively nomenclated as:

N-(9-Methyl-9H-carbazol-3-yl)-2-[4-(2-oxo-4H-benzo[d][1,3]oxazin-1-yl)-piperidin-1-yl]-acetamide hydrochloride

[26] 1-{1-[N-(2-anthraquinoyl)aminocarbonylmethyl]-4-(piperidinyl)}-1,4-dihydro-2H-3,1-benzoxazin-2-one hydrochloride, alternatively nomenclated as:

N-(9,10-Dioxo-9,10-dihydro-anthracen-2-yl)-2-[4-(2-oxo-4H-benzo[d][1,3]oxazin-1-yl)-piperidin-1-yl]-acetamide hydrochloride

[27] 1-{1-[N-(4-(N-ethyl-N-phenylamino)phenyl)aminocarbonylmethyl]-4-(piperidinyl)}-1,4-dihydro-2 H-3,1-benzoxazin-2-one hydrochloride, alternatively nomenclated as:

N-[4-(Ethyl-phenyl-amino)-phenyl]-2-[4-(2-oxo-4H-benzo[d][1,3]oxazin-1-yl)-piperidin-1-yl]-acetamide hydrochloride

[28] 1-{1-[N-(4-(N-ethyl-N-phenylamino)phenyl)aminocarbonylmethyl]-4-(piperidinyl)}-6-methyl-1,4-dihydro-2H-3,1-benzoxazin-2-one hydrochloride, alternatively nomenclated as:

2-[4-(6-Methyl-2-oxo-4H-benzo[d][1,3]oxazin-1-yl)-piperidin-i -yl]-N-[4-methyl-phenyl-amino)-phenyl]-acetamide hydrochloride

[29] 1-{1-[N-(4-phenyloxyphenyl)aminocarbonylmethyl]-4-(piperidinyl)}-1,4-dihydro-2H-3,1-benzoxazin-2-one hydrochloride, alternatively nomenclated as:

2-[4-(2-oxo-4H-benzo[d][1,3]oxazin-1-yl)-piperidin-1-yl]-N-[4-phenoxy-phenyl]-acetamide hydrochloride

[30] 1-{1-[N-(4-(N-isopropyl-N-phenylamino)phenyl)aminocarbonylmethyl]-4-(piperidinyl)}-1,4-dihydro-2H-3,1-benzoxazin-2-one hydrochloride, alternatively nomenclated as:

N-[4-(lsopropyl-phenyl-amino)-phenyl]-2-[4-(2-oxo-4H-benzo[d][1,3]oxazin-1-yl)-piperidin-1-yl]-acetamide hydrochloride

[31] 1-{1-[N-(9-oxo-9H-fluoren-3-yl)aminocarbonylethyl]-4-(piperidinyl)}-1,4-dihydro-2H-3,1-benzoxazin-2-one hydrochloride, alternatively nomenclated as:

3-[4-(2-Oxo-4H-benzo[d][1,3]oxazin-1-yl)-piperidin-1-yl]-N-(9-oxo-9H-fluoren-3-yl)-propionamide hydrochloride

[32] 1-{1-[ N-(9-ethyl-9H-carbazol-3-yl)aminocarbonylmethyl]-4-(piperidinyl)}-6-chloro-1,4-dihydro-2H-3,1-benzoxazin-2-one hydrochloride, alternatively nomenclated as:

2-[4-(6-Chloro-2-oxo-4H-benzo[d][1,3]oxazin-1-yl)-piperidin-1-yl]-N-(9-ethyl-9H-carbazol-3-yl)-acetamide hydrochloride

[33] 1-{1-[N-(4-chlorophenyl)aminocarbonylmethyl]-4-(piperidinyl)}-1,4-dihydro-2H-3,1-benzoxazin-2-one hydrochloride, alternatively nomenclated as:

N-(4-Chloro-phenyl)-2-[4-(2-oxo-4H-benzo[d][1,3]oxazin-1-yl)-piperidin-1-yl]-acetamide hydrochloride

[34] 1-{1-[N-(4-chlorophenyl)aminocarbonylmethyl]-4-(piperidinyl)}-6-chloro-1,4-dihydro-2H-3,1-benzoxazin-2-one hydrochloride, alternatively nomenclated as:

2-[4-(6-Chloro-2-oxo-4H-benzo[d][1,3]oxazin-1-yl)-piperidin-1-yl]-N-(4-chloro-phenyl)-acetamide hydrochloride

[35] 1-{1-[N-(9-oxo-9H-fluoren-3-yl)aminocarbonylmethyl]-4-(piperidinyl)}-8-methyl-1,4-dihydro-2H-3,1-benzoxazin-2-one hydrochloride, alternatively nomenclated as:

2-[4-(8-Methyl-2-oxo-4H-benzo[d][1,3]oxazin-1-yl)-piperidin-1-yl]-N-(9-oxo-9H-fluoren-3-yl)-acetamide hydrochloride

[36] 1-{1-[N-(9-oxo-9H-fluoren-3-yl)aminocarbonylmethyl]-4-(piperidinyl)}-6-chloro-1,4-dihydro-2H-3,1-benzoxazin-2-one hydrochloride, alternatively nomenclated as:

2-[4-(6-Chloro-2-oxo-4H-benzo[d][1,3]oxazin-1-yl)-piperidin-1-yl]-N-(9-oxo-9H-fluoren-3-yl)-acetamide hydrochloride

[37] 1-{1-[N-(1-hydroxy-9H-fluoren-3-yl)aminocarbonylmethyl]-4-(piperidinyl)}-8-methyl-1,4-dihydro-2H-3,1-benzoxazin-2-one hydrochloride, alternatively nomenclated as:

N-(9-Hydroxy-9H-fluoren-3-yl)-2-[4-(8-methyl-2-oxo-4H-benzo[d][1,3]oxazin-1-yl)-piperidin-1-yl]-acetamide hydrochloride

[38] 1-{1-[N-(1-hydroxy-9H-fluoren-2-yl)aminocarbonylmethyl]-4-(piperidinyl)}-1,4-dihydro-2H-3,1-benzoxazin-2-one hydrochloride, alternatively nomenclated as:

N-(9-Hydroxy-9H-fluoren-2-yl)-2-[4-(2-oxo-4H-benzo[d][1,3]oxazin-1-yl)-piperidin-1-yl]-acetamide hydrochloride

[39] 1-{1-[N-(1-hydroxy-9H-fluoren-3-yl)aminocarbonylmethyl]-4-(piperidinyl)}-6-chloro-1,4-dihydro-2H-3,1-benzoxazin-2-one hydrochloride, alternatively nomenclated as:

2-[4-(6-Chloro-2-oxo-4H-benzo[d][1,3]oxazin-1-yl)-piperidin-1-yl]-N-(9-hydroxy-9H-fluoren-3-yl)-acetamide hydrochloride

[40] 1-{1-[ N-(9-ethyl-9H-carbazol-3-yl)aminocarbonylmethyl]-4-(piperidinyl)}-8-methyl-1,4-dihydro-2H-3,1-benzoxazin-2-one hydrochloride, alternatively nomenclated as:

N-(9-Ethyl-9H-carbazol-3-yl)-2-[4-(8-methyl-2-oxo-4H-benzo[d][1,3]oxazin-1-yl)-piperidin-1-yl]-acetamide hydrochloride

[41] 2-[4-(8-Methyl-2-oxo-4H-benzo[d][1,3]oxazin-1-yl)-piperidin-1-yl]-N-(4-trifluoro-methyl-phenyl)-acetamide hydrochloride,

[42] 2-[4-(8-Methyl-2-oxo-4H-benzo[d][1,3]oxazin-1-yl)-piperidin-1-yl-]-N-phenyl-acetamide hydrochloride,

[43] 2-[4-(2-oxo-4H-benzo[d][1,3]oxazin-1-yl)-piperidin-1-yl]-N-(4trifluoromethyl-phenyl)-acetamide hydrochloride,

[44] 2-[4-(6-Chloro-2-oxo-4H-benzo[d][1,3]oxazin-1-yl)-piperidin-1-yl]-N-phenyl-acetamide hydrochloride,

[45] 2-[4-(6-Chloro-2-oxo-4H-benzo[d][1,3]oxazin-1-yl)-piperidin-1-yl]-N-(4-trifluoromethyl-phenyl)-acetamide hydrochloride,

[46] 2-[4-(2-oxo-4H-benzo[d][1,3]oxazin-1-yl)-piperidin-1-yl]-N-phenyl-acetamide-hydrochloride,

[47] N-(4-Chloro-phenyl)-2-[4-(8-Methyl-2-oxo-4H-benzo[d][1,3]oxazin-1-yl)-piperidin-1-yl]-acetamide hydrochloride,

[48] N-(4-Cyano-phenyl)-2-[4-(2-oxo-4H-benzo[d][1,3]oxazin-1-yl)-piperidin-1-yl-]-acetamide hydrochloride,

[49] N-(4-Cyano-phenyl)-2-[4-(8-methyl-2-oxo-4H-benzo[d][1,3]oxazin-1-yl)-piperidin-1-yl]-acetamide hydrochloride,

[50] 2-[4-(6-Chloro-2-oxo-4H-benzo[d][1,3]oxazin-1-yl)-piperidin-1-yl]-N(4-cyano-phenyl)-acetamide hydrochloride,

[51] N-(4-Acetyl-phenyl)-2-[4-(2-oxo-4H-benzo[d][1,3]oxazin-1-yl)-piperidin-1-yl]-acetamide hydrochloride,

[52] 2-[4-(8-Methyl-2-oxo-4H-benzo[d][1,3]oxazin-1-yl)-piperidin-1-yl]-N4-phenoxy-phenyl)-acetamide hydrochloride,
[53] N-(4-Acetyl-phenyl)-2-[4-(6-chloro-2-oxo-4H-benzo[d][1,3]oxazin-1-yl)-piperidin-1-yl]-acetamide hydrochloride,
[54] N-(4-Acetyl-phenyl)-2-[4-(8-methyl-2-oxo-4H-benzo[d][1,3]oxazin-1-yl)-piperidin-1-yl]-acetamide hydrochloride,
[55] 2-[4-(6-Chloro-2-oxo-4H-benzo[d][1,3]oxazin-1-yl)-piperidin-1-yl]-N-(4)-phenyl)-acetamide hydrochloride,
[56] N-(4-Benzoyl-phenyl)-2-[4-(8-methyl-2-oxo-4H-benzo[d][1,3]oxazin-1-yl-piperidin-1-yl]-acetamide hydrochloride,
[57] N-(4-Benzoyl-phenyl)-2-[4-(6-chloro-2-oxo-4H-benzo[d][1,3]oxazin-1-yl-piperidin-1-yl]-acetamide hydrochloride,
[58] N-(2-Chloro-phenyl)-2-[4-(6-methyl-2-oxo-4H-benzo[d][1,3]oxazin-1-yl)-piperidin-1-yl]-acetamide,
[59] 2-[4-(6-Methyl-2-oxo-4H-benzo[d][1,3]oxazin-1-yl)-piperidin-1yl]-N-(2-trifluoromethyl-phenyl)-acetamide,
[60] 2-[4-(6-Methyl-2-oxo-4H-benzo[d][1,3]oxazin-1-yl)-piperidin-1-yl]-N-phenyl-acetamide,
[61] N-(4-Cyclohexyl-phenyl)-2-[4-(8-methyl-2-oxo-4H-benzo[d][1,3]oxazin-1-yl)-piperidin-1-yl]-acetamide hydrochloride,
[62] 2-[4-(6-Chloro-2-oxo-4H-benzo[d][1,3]oxazin-1-yl)-piperidin-1-yl]-N-(4-cyclohexyl-phenyl)-acetamide hydrochloride,
[63] N-(2-Benzoyl-phenyl)-2-[4-(2-oxo-4H-benzo[d][1,3]oxazin-1-yl)-piperidin-1-yl]-acetamide hydrochloride,
[64] N-(2-Benzoyl-phenyl)-2-[4-(8-methyl-2-oxo-4H-benzo[d][1,3]oxazin-1-yl-piperidin-1-yl]-acetamide hydrochloride,
[65] N-(2-Benzoyl-phenyl)-2-[4-(6-chloro-2-oxo-4H-benzo[d][1,3]oxazin-1-1-yl)-piperidin-1-yl]-acetamide hydrochloride,
[66] N-(2-Benzoyl-phenyl)-2-[4-(6-methyl-2-oxo-4H-benzo[d][1,3]oxazin-1-yl)-piperidin-1-yl]-acetamide,
[67] 2-[4-(6-Methyl-2-oxo-4H-benzo[d][1,3]oxazin-1-yl)-piperidin-1-yl]-phenoxy-phenyl)-acetamide hydrochloride,
[68] N-(4-Acetyl-phenyl)-2-[4-(6-methyl-2-oxo-4H-benzo[d][1,3]oxazin-1-yl)-piperidin-1-yl]-acetamide hydrochloride,
[69] N-(9-Hydroxy-9H-fluoren-3-yl)-2-[4-(2-oxo-4H-benzo[d][1,3]oxazin-1-yl)-piperidin-1-yl]-acetamide hydrochloride,
[70] 2-[4-(6-Chloro-2-oxo-4H-benzo[d][1,3]oxazin-1-yl)-piperidin-1-yl]-N-(9-oxo-9H-fluoren-2-yl)-acetamide hydrochloride,
[71] 2-[4-(6-Methyl-2-oxo-4H-benzo[d][1,3]oxazin-1-yl)-piperidin-1-yl]-N-(9-oxo-9H-fluoren-2-yl)-acetamide hydrochloride,
[72] 2-[4-(8-Methyl-2-oxo-4H-benzo[d][1,3]oxazin-1-yl)-piperidin-1-yl]N-(9oxo-9H-fluoren-2-yl)-acetamide hydrochloride,
[73] 2-[4-(6-Chloro-2-oxo-4H-benzo[d][1,3]oxazin-1-yl)-piperidin-1-1]-N-(9-hydroxy-9H-fluoren-2-yl)-acetamide hydrochloride,
[74] N-(9-Hydroxy-9H-fluoren-2-yl)-2-[4-(6-methyl-2-oxo-4H-benzo[d][1,3]oxazin-1-yl)-piperidin-1-yl]-acetamide hydrochloride,
[75] N-(9-Hydroxy-9H-fluoren-2-yl)-2-[4-(8-methyl-2-oxo-4H-benzo[d][1,3 oxazin-1-yl)-piperidin-1-yl]-acetamide hydrochloride,
[76] N-(9-Hydroxy-9H-fluoren-3-yl)-2-[4-(6-methyl-2-oxo-4H-benzo[d][1,3]oxazin-1-yl)-piperidin-1-yl]-acetamide hydrochloride,
[77] N-(4-Cyclohexyl-phenyl)-2-[4-(7-fluoro-2-oxo-4H-benzo[d][1,3]oxazin-1-yl)-piperidin-1-yl]-acetamide hydrochloride,
[78] N-(9-Ethyl-9H-carbazol-3-yl)-2-[4-(5-fluoro-2-oxo-4H-benzo[d][1,3]oxazin-1-yl)-piperidin-1-yl]-acetamide hydrochloride,
[79] N-(9-Ethyl-9H-carbazol-3-yl)-2-[4-(6-methoxy-2-oxo-4H-benzo[d][1,3]oxazin-1-yl)-piperidin-1-yl]-acetamide hydrochloride,
[80] N-(9-Ethyl-9H-carbazol-3-yl)-2-[4-(7-methyl-2-oxo-4H-benzo[d][1,3]oxazin-1-yl)-piperidin-1-yl]-acetamide hydrochloride,
[81] 2-[4-(5-Chloro-2-oxo-4H-benzo[d][1,3]oxazin-1-yl)-piperidin-1-yl]-N-(9-ethyl-9H-carbazol-3-yl)acetamide hydrochloride,
[82] 2-[4-(5-Fluoro-2-oxo-4H-benzo[d][1,3]oxazin-1-yl)-piperidin-1-yl]-N-(9-oxo-phenoxy-phenyl)-acetamide hydrochloride,
[83] 2-[4-(6-methoxy-2-oxo-4H-benzo[d][1,3]oxazin-1-yl)-piperidin-1-yl]-N-(9-oxo-9H-fluoren-3-yl)-acetamide,
[84] N-Dibenzofuran-2-yl-2-[4-(8-methoxy-2-oxo-4H-benzo[d][1,3]oxazin-1yl)-piperidin-1-yl]-acetamide,
[85] 2-[4-(7-Chloro-2-oxo-4H-benzo[d][1,3]oxazin-1-yl)-piperidin-1-yl]-N-dibenzofuran-2-yl-acetamide,
[86] 2-[4-(6-Fluoro-2-oxo-4H-benzo[d][1,3]oxazin-1-yl)-piperidin-1-yl]-N-(9-oxo-9H-fluoren-3-yl)-acetamide,
[87] 2-[4-(7-Fluoro-2-oxo-4H-benzo[d][1,3]oxazin-1-yl)-piperidin-1-yl]-N-(9-hydroxy-9H-fluoren-3-yl)-acetamide,
[88] N-(9H-Carbazol-3-yl)-2-[4-(5-methyl-2-oxo-4H-benzo[d][1,3]oxazin-1-yl)-piperidin-1-yl]-acetamide,
[89] N-(9H-Carbazol-3-yl)-2-[4-(5-fluoro-2-oxo-4H-benzo[d][1,3]oxazin-1-yl)-piperidin-1-yl]-acetamide,
[90] N-(9H-carbazol-3-yl)-2-[4-(6-methoxy-2-oxo-4H-benzo[d][1,3]oxazin-1-yl)-piperidin-1-yl]-acetamide,
[91] N-(9-Ethyl-9H-carbazol-3-yl)-2-[4-(5-methoxy-2-oxo-4H-benzo[d][1,3oxazin-1-yl)-piperidin-1-yl]-acetamide,
[92] 2-[4-(5-Methoxy-2-oxo-4H-benzo[d][1,3]oxazin-1-yl)-piperidin-1-yl]-N-(4-phenoxy-phenyl)-acetamide,
[93] N-(9-Hydroxy-9H-fluoren-3-yl)-2-[4-(7-methyl-2-oxo-4H-benzo[d][1,3oxazin-1-yl)-piperidin-1-yl]-acetamide,
[94] N-(9-Hydroxy-9H-fluoren-3-yl)-2-[4-(8-methoxy-2-oxo-4H-benzo[d][1,3]oxazin-1-yl)-piperidin-1-yl]-acetamide,
[95] N-Dibenzofuran-2-yl-2-[4-(5-methyl-2-oxo-4H-benzo[d][1,3]oxazin-1-yl)-piperidin-1-yl]-acetamide,
[96] N-[4-(Ethyl-phenyl-amino)-phenyl]-2-[4-(7-methyl-2-oxo-4H-benzo[d][1,3]oxazin-1-yl)-piperidin-1-yl]-acetamide,
[97] N-(9H-Carbazol-3-yl)-2-[4-(8-chloro-2-oxo-4H-benzo[d][1,3]oxazin-1-yl)-piperidin-1-yl]-acetamide,
[98] N-[4-(Ethyl-phenyl-amino)-phenyl]-2-[4-(8-methoxy-2-oxo-4H-benzo[d][1,3]oxazin-1-yl)-piperidin-1-yl]-acetamide,
[99] N-(9-Hydroxy-9H-fluoren-4-yl)-2-[4-(2-oxo-4H-benzo[d][1,3]oxazin-1-yl)-piperidin-1-yl]-acetamide,
[100] N-[4-(Hydroxy-phenyl-methyl)-phenyl-2-[4-(2-oxo-4H-benzo[d][1,3]oxazin-1-yl)-piperidin-1-yl]-acetamide, The intermediates of general formulas (VI) and (VII) are prepared by means of conventional organic chemistry methods. As an example not limiting in any way the scope of the present invention, the preparation of some of the intermediates of general formula (VII) is shown below:

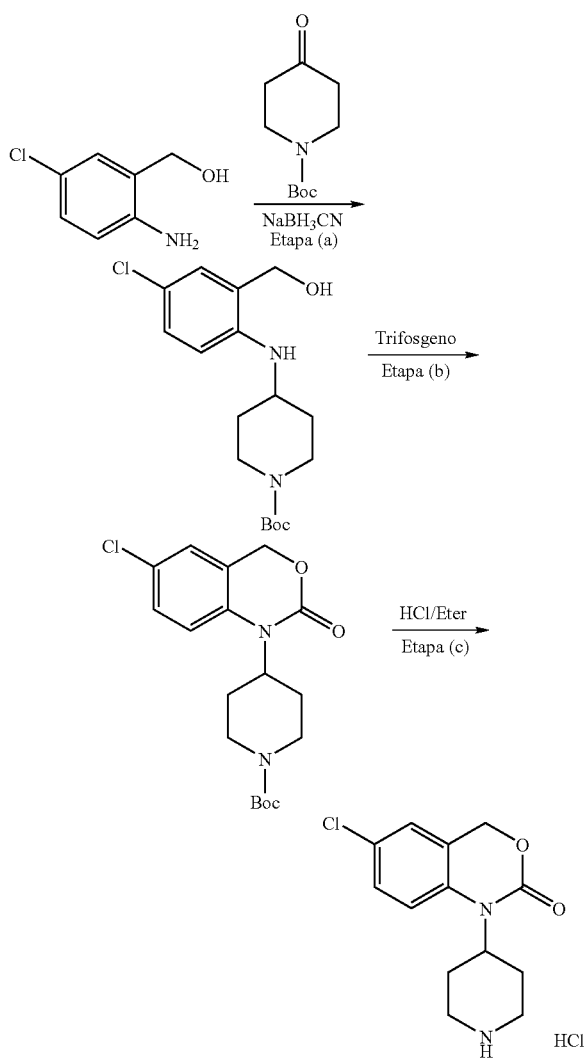

Stage a) 1-(tert-Butyloxycarbonyl)-4-[4-chloro-(2-hydroxymethylphenylamino)] piperidine A solution of 1-(tert-butyloxycarbonyl)-4-piperidinone (20 g, 0.10 mol), 2-amino-5-chlorobenzyl alcohol (17.34 g, 0.11 mol) and acetic acid (14 mL, 0.22 mol) in dry toluene (500 mL) was heated at reflux temperature, with water elimination by means of azeotrope distillation with a Dean-Stark device, for 6 hours. The mixture was then cooled and vacuum concentrated up to half volume. NaBH$_3$CN (20 g, 0.32 mol) and dry THF (300 mL) were added to the resulting solution. Acetic acid (10 mL, 0.17 mol) was then dripped for one hour. The reaction was stirred at room temperature for 24 hours. The mixture was vacuum concentrated and the residue was dissolved in ethyl acetate (750 mL), washed with a NaHCO$_3$-saturated solution (4×250 mL) and a NaCl-saturated solution (250 mL), dried and evaporated to dryness. The residue was purified by means of flash chromatography eluting with a mixture of ethyl acetate:petroleum ether (1:3). The desired product was thus obtained as an oil (32.7 g, 96%).

$^1$H NMR (CDCl$_3$): 1.32 (d, J=11.2 Hz, 2H), 1.41(s, 9H), 1.92 (d, J=11.2 Hz, 2H), 2.92 (t, J=12.0 Hz, 1H), 3.10 (s, 1H), 3.37 (m, 1H), 3.88 (d, J=13.7 Hz, 2H), 4.49 (s, 2H), 4.75 (s, 1H), 6.52 (d, J=8.6 Hz, 1H), 6.96 (s, 1H), 7.07 (d, J=8.6 Hz, 1H).

Stage b) 1-(1-tert-Butyloxycarbonyl-4-piperidinyl)-6-chloro-1,4-dihydro-2H-3,1-benzoxazin-2-one N,N-diisopropylethylamine (DIEA) (43 mL, 0.25 mol) and triphosgene (8.65 g, 29.2 mmol) were added to a solution of 1-(tert-Butyloxycarbonyl)-4-[(4-chloro-(2-hydroxymethyl)phenyl-amino)]piperidine (27.0 g, 79 mmol) in dry THF (250 mL) cooled at 0° C. The reaction was stirred at 0° C. for 1 h and at room temperature for 72 h. Ethyl ether was added and the mixture was cooled at 0° C. for 3 h and the DIEA hydrochloride was then filtered. The filtered solution was evaporated to dryness and the residue was dissolved in ethyl acetate (750 mL), washed with 5% solution of citric acid (2×500 mL), water (250 mL) and NaHCO$_3$-saturated solution (2×500 mL). The ethyl acetate solution was dried (MgSO$_4$), filtered and evaporated under reduced pressure. The residue was brought to the boil with ethyl ether until the whole solid was dissolved and then cooled overnight to yield the desired compound in crystalline form (28.9 g, 67%).

Melting point: 177–179° C. $^1$H NMR (CDCl$_3$): 1.46 (s, 9H), 1.79 (d, J=10.1 Hz, 1H), 2.54 (m, 2H), 2.78 (m, 2H), 3.96 (m, 1H), 4.28 (m, 2H), 5.02 (s, 2H), 6.98 (d, J=8.7 Hz, 1H), 7.13 (d, J=2.4 Hz, 1H), 7.28 (dd, J=8.7 Hz, J=2.4 Hz, 1H).

Stage c) 6-chloro-1-(piperidin-4-yl)-1,4-dihydro-2H-3,1-benzoxazin-2-one hydrochloride A solution of 1-[(1-tert-Butyloxycarbonyl)-4-piperidinyl]-6-chloro-1,4-dihydro-2H-3,1-benzoxazin-2-one (24 g, 65 mmol) in ethyl acetate (500 mL) was cooled at 0° C. A 5 M solution of hydrogen chloride in ethyl ether (500 mL) was then added and the resulting mixture was stirred at 0° C. for 4 h. The precipitate formed was collected by filtration, washed with ether and vacuum dried to yield the desired product as a solid (16.95 g, 97%).

Melting point: 254–257° C. $^1$H NMR (CD$_3$OD): 2.13 (d, J=12.2 Hz, 2H), 2.88 (m, 2H), 3.20 (m, 2H), 3.53 (d, J=12.8 Hz, 2H), 4.24 (m, 1H), 5.16 (s, 2H), 7.31 (m, 2H), 7.41 (dd, J=8.8 Hz, J=2.6 Hz, 1H).

From the corresponding anthranilic acids, by reduction with lithium hydride and aluminum and other conventional methods, the benzylalcohol derivatives are prepared that are used as a starting point for obtaining the various substituted 3,1-benzoxazin-2-ones by a procedure analogous to that previously described. The following substituted 3,1-benzoxazin-2-ones with the formula VII are not known in the state of the art:

6-methyl-1-(piperidin-4-yl)-1,4-dihydro-2H-3,1-benzoxazin-2-one,
7-methyl-1-(piperidin-4-yl)-1,4-dihydro-2H-3,1-benzoxazin-2-one,
8-methyl-1-(piperidin-4-yl)-1,4-dihydro-2H-3,1-benzoxazin-2-one,
5-chloro-1-(piperidin-4-yl)-1,4-dihydro-2H-3,1-benzoxazin-2-one,
6-chloro-1-(piperidin-4-yl)-1,4-dihydro-2H-3,1-benzoxazin-2-one,
8-chloro-1-(piperidin-4-yl)-1,4-dihydro-2H-3,1-benzoxazin-2-one,
6-fluoro-1-(piperidin-4-yl)-1,4-dihydro-2H-3,1-benzoxazin-2-one, 7-fluoro-1-(piperidin-4-yl)-1,4-dihydro-2H-3,1-benzoxazin-2-one, 5-methoxy-1-(piperidin-4-yl)-1,4-dihydro-2H-3,1-benzoxazin-2-one, 6-methoxy-1-(piperidin-4-yl)-1,4-dihydro-2H-3,1-benzoxazin-2-one, 5-hydroxy-1-(piperidin-4-yl)-1,4-dihydro-2H-3,1-benzoxazin-2-one, 6-hydroxy-1-(piperidin-4-yl)-1,4-dihydro-2H-3,1-benzoxazin-2-one, and 8-hydroxy-1-(piperidin-4-yl)-1,4-dihydro-2H-3,1-benzoxazin-2-one The lack of protection of the corresponding 5-methoxy-1-(piperidinyl)-1,4-dihydro-2H-3,1-benzoxazin-2-one, 8-methoxy-1-(piperidinyl)-1,4-dihydro-2H-3,1-benzoxazin-2-one and 6-methoxy-1-(piperidinyl)-1,4-dihydro-2H-3,1-benzoxazin-2-one by conventional methods, such as $BBr_3$ in an inert organic solvent leads to the corresponding derivatives 5-hydroxy-1-(piperidinyl)-1,4-dihydro-2H-3,1-benzoxazin-2-one, 8-hydroxy-1-(piperidinyl)-1,4-dihydro-2H-3,1-benzoxazin-2-one and 6-hydroxy-1-(piperidinyl)-1,4-dihydro-2H-3,1-benzoxazin-2-one. The unsubstituted benzoxazin-2-one, 1-(piperidin-4-yl)-1,4-dihydro-2H-3,1-benzoxazin-2-one, was prepared according to the procedure described in the literature (*J. Med. Chem.* 1995, 38, 4634) y (*J. Med. Chem.* 1998, 41,2146).

Reduction of the Substituted Anthranilic Acids:

The substituted anthranilic acids were reduced in standard conditions using $LiAlH_4$ as a reducing agent, in anhydrous THF in an inert atmosphere. The process is very efficient and in most cases the corresponding 2-aminobenzylalcohols are obtained with good yields.

Experimental Data:

100 mL of anhydrous THF and 116.6 mmoles of $LiAlH_4$ were introduced in a three-neck flask provided with mechanical stirring and a nitrogen atmosphere. The suspension was cooled to 0° C. and a solution of 58.3 mmoles of the corresponding substituted anthranilic acid in 150 mL of anhydrous THF was added on it. The reaction mixture was heated to ambient temperature and stirred for one hour. With external cooling to 0° C., 4.7 mL of water, 4.7 mL of NaOH 15%, and finally 14 mL of water were added carefully. The suspension was filtered and the precipitate washed with ethyl acetate. The organic phase was washed with water, dried and evaporated. In most cases the crude can be used without subsequent purification.

Biological Assays

Binding to Neuropeptide $Y_5$

The experimental protocol follows the method by M. Gobbi et al. [M. Gobbi, T. Mennini, A. Vezzani: Autoradiographic Reevaluation of the Binding Properties of [$^{125}$I][Leu$^{31}$, Pro$^{34}$]Peptide YY and [$^{125}$I]Peptide YY$_{3-36}$ to Neuropeptide Y Receptor Subtypes in Rat Forebrain. *The Journal of Neurochemistry*, 1999, 72, 1663–1670], with modifications. Male Wistar rats are sacrificed by decapitation, their brains are rapidly removed and the cortex is dissected. Homogenization is performed in cold conditions in the buffer: 120 mM NaCl, 4.7 mM KCl, 2.2 mM $CaCl_2$, 1.2 mM $KH_2PO_4$, 1.2 mM $MgSO_4$, 25 mM $NaHCO_3$, 5.5 mM glucose, pH 7.4, by means of a Ultra-Turrax homogenizer for 15 seconds at 13,500 rpm. The ratio between fresh tissue weight and buffer volume is of twenty times. The membrane is centrifuged for 10 min at 48,000 g. The supernatant is discarded and the pellet is washed, resuspended and recentrifuged three more times. The final membrane resuspension is performed in the buffer: 120 mM NaCl, 4.7 mM KCl, 2.2 mM $CaCl_2$, 1.2 mM $KH_2PO_4$, 1.2 mM $MgSO_4$, 25 mM $NaHCO_3$, 5.5 mM glucose, 0.1% BSA, 0.05% bacitracin, pH 7.4, at a ratio of 20 ml/g fresh tissue. The radioligand used is [$^{125}$I]-PYY$_{3-36}$ at the concentration of 28 μM. Incubation volume: 500 μl. A 1 μM concentration of BIBP 3226 is added to the incubation medium in order to saturate receptor $Y_1$. Incubation is performed at 25° C. for 120 minutes and ended by rapid filtration in a Harvester Brandel Cell through fiberglass filters of the brand Schleicher & Schuell GF 3362 pretreated with a 0.5% polyethylenimine solution. The filters are cold-washed three times with two milliliters of the same buffer used in homogenization. The filters are transferred to vials and 5 ml of Ecoscint H liquid scintillation cocktail are added to each vial. The vials are allowed to reach steady state for a few hours before counting in a Wallac Winspectral 1414 scintillation counter. Non-specific binding is determined in the presence of 1 μM of pNPY (porcin Neuropeptide Y). The assays are performed in triplicate.

Binding to Neuropeptide $Y_2$

The experimental protocol follows the method by Y. Dumont et al. [Y. Dumont, A. Fournier, S. St-Pierre, R. Quirion: Characterization of Neuropeptide Y Binding Sites in Rat Brain Preparations Using [$^{125}$I][Leu$^{31}$, Pro$^{34}$]Peptide YY and [$^{125}$I]Peptide YY$_{3-36}$ as Selective Y1 and Y2 Radioligands. *The Journal of Pharmacology and Experimental Therapeutics*, 1995, 272, 673–680], with slight modifications. Male Wistar rats are sacrificed by decapitation, their brains are rapidly removed and the hypoccampus is dissected. Homogenization is performed in cold conditions in the buffer: 120 mM NaCl, 4.7 mM KCl, 2.2 mM $CaCl_2$, 1.2 mM $KH_2PO_4$, 1.2 mM $MgSO_4$, 25 mM $NaHCO_3$, 5.5 mM glucose, pH 7.4, by means of a Ultra-Turrax homogenizer for 15 seconds at 13,500 rpm. The ratio between fresh tissue weight and buffer volume is of ten times. The membrane is centrifuged for 10 min at 48,000 g. The supernatant is discarded and the pellet is washed, resuspended and recentrifuged two more times. The final membrane resuspension is performed in the buffer: 120 mM NaCl, 4.7 mM KCl, 2.2 mM $CaCl_2$, 1.2 mM $KH_2PO_4$, 1.2 mM $MgSO_4$, 25 mM $NaHCO_3$, 5.5 mM glucose, 0.1% BSA, 0.05% bacitracin, pH 7.4, at a ratio of 90 ml/g fresh tissue. The radioligand used is [$^{125}$I]-PYY$_{3-36}$ at the concentration of 28 μM. Incubation volume: 500 μl. Incubation is performed at 25° C. for 150 minutes and ended by rapid filtration in a Harvester Brandel Cell through fiberglass filters of the brand Schleicher & Schuell GF 3362 pretreated with a 0.5% polyethylenimine solution. The filters are cold-washed three times with three milliliters of the same buffer used in homogenization. The filters are transferred to vials and 5 ml of Ecoscint H liquid scintillation cocktail are added to each vial. The vials are allowed to reach steady state for a few hours before counting in a Wallac Winspectral 1414 scintillation counter. Non-specific binding is determined in the presence of 1 μM of pNPY (porcin Neuropeptide Y). The assays are performed in triplicate.

| Example | Neuropeptide $Y_5$ Binding [$^{125}$I]-PYY$_{(3-36)}$ BIBP 3226 sat. Rat cortex $K_i$ (nM) | Neuropeptide $Y_2$ Binding [$^{125}$I]-PYY$_{(3-36)}$ Rat hypoccampus $K_i$ (nM) |
|---|---|---|
| 3 | 6.4 | >1000 |

| Example | Neuropeptide $Y_5$ Binding [$^{125}$I]-PYY$_{(3-36)}$ BIBP 3226 sat. Rat cortex $K_i$ (nM) | Neuropeptide $Y_2$ Binding [$^{125}$I]-PYY$_{(3-36)}$ Rat hypoccampus $K_i$ (nM) |
|---|---|---|
| 4 | 7.3 | >1000 |
| 5 | 8.3 | >1000 |
| 6 | 18.4 | >1000 |
| 18 | 3.4 | >1000 |
| 20 | 0.87 | >1000 |

Measurement of the Intake in Animal Models

The animals employed were male Wistar rats (200–270 g) supplied by Harlan, S. A. The acclimatization period in our stable before being used in the experimental trials was at least 5 days. In this time the animals were stabled in groups of 5 in translucid cages, with water and food ad libitum. The animals were acclimatized to individual stabling at least 24 hours before conducting the experiment.

Nocturnal Ingestion Test

The test is carried out in the animal's cage in order to minimize the stress implied in a change of cage, which could affect the intake. Water and food are available at all times ad libitum. Immediately before turning out the lights in the room the animals are weighed and randomly assigned to a treatment group (vehicle or product under study). Immediately after the administration the rats are returned to their cages, where a known amount of food had been placed. The following morning the amount of food remaining in each cage was weighed, and the animals were again weighed.

References: Ants Kask et al., *Journal of Pharmacology*, 414 (2001) 215–224; Andrew V. Turnbull et al., *Diabetes*, Vol. 51, August 2002

Effect of Some Compounds of the Invention on Nocturnal Ingestion in Male Wistar Rats (Intra-Peritoneal Administration)

| EXAMPLE | DOSE (mg/kg) | EFFECT |
|---|---|---|
| 20 | 40 | Reduces food intake and reduces body weight of the animals treated compared to those of the control group. |
| 18 | 40 | Reduces food intake and reduces body weight of the animals treated compared to those of the control group. |
| 35 | 20 | Reduces food intake and reduces body weight of the animals treated compared to those of the control group. |

Dosage

The daily dosage in human medicine ranges between 1 milligram and 500 milligrams of substance, to be administered in one or several intakes. The compositions are prepared in forms compatible with the administration route used, e.g. tablets, pills, capsules, suppositories, solutions or suspensions. These compositions are prepared by means of well-known methods and include between 1 to 60% by weight of active substance (compound of general formula I) and 40 to 99% by weight of appropriate pharmaceutical vehicle compatible with the active substance and the physical form of the composition used. The formula of a tablet containing one product of the invention is shown as an example.

Example of Formula Per Tablet

| Example 18 | 5 mg |
|---|---|
| Lactose | 60 mg |
| Crystalline cellulose | 25 mg |
| Povidone K 90 | 5 mg |
| Pregelanitized starch | 3 mg |
| Colloidal silica dioxide | 1 mg |
| Magnesium stearate | 1 mg |
| Total weight per tablet | 100 mg |

The invention claimed is:

1. A benzoxazinone-derived compound of formula (I)

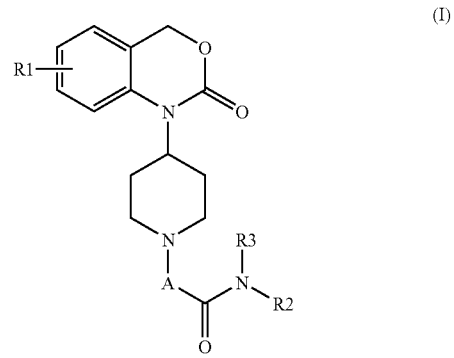

wherein:
$R_1$ represents hydrogen, halogen, alkoxy or a $C_1$–$C_4$ alkyl;
$R_2$ represents hydrogen, a $C_1$–$C_4$ alkyl, a phenyl, a benzyl or together with $R_3$ along with the N atom to which they are attached may be part of a five- or 6-member heterocycle;
$R_3$ represents a substituted or non-substituted bicyclic ring, a substituted or non-substituted tricyclic ring, phenyl substituted or phenyl substituted by a hydrocarbonated chain which together with $R_2$ along with the N atom to which they are attached is part of a 5 or 6-member nitrogenous heterocycle;
A represents —CHR$_4$— or —CHR$_4$—CH$_2$—; and
$R_4$ represents hydrogen, a $C_1$–$C_4$ alkyl or a phenyl;
or one of its physiologically acceptable salts, selected among the group:
[1] 2-[4-(2-oxo-4H-benzo[d][1,3]oxazin-1-yl)-piperidin-1-yl]-N-(9-oxo-9H-fluoren-2-yl)-acetamide,
[2] 2-[4-(2-oxo-4H-benzo[d][1,3]oxazin-1-yl)-piperidin-1-yl]-N-(9-oxo-9H-fluoren-3-yl)-acetamide,
[3] 2-[4-(2-oxo-4H-benzo[d][1,3]oxazin-1-yl)-piperidin-1-yl]-N-(9-oxo-9H-fluoren-3-yl)-acetamide hydrochloride,
[4] N-(4-benzoyl-phenyl)-2-[4-(2-oxo-4H-benzo[d][1,3] oxazin-1-yl)-piperidin-1-yl]-acetamide,
[5] N-(4-benzoyl-phenyl)-2-[4-(2-oxo-4H-benzo[d][1,3] oxazin-1-yl)-piperidin-1-yl]-acetamide hydrochloride,
[6] 2-[4-(2-oxo-4H-benzo[d][1,3]oxazin-1-yl)-piperidin-1-yl]-N-(5-oxo-5,6,7,8-tetrahydro-naphtalen-2-yl)-acetamide hydrochloride,
[7] 2-[4-(2-oxo-4H-benzo[d][1,3]oxazin-1-yl)-piperidin-1-yl]-N-(9-oxo-9H-fluoren-4-yl)-acetamide hydrochloride,
[8] N-(3-benzoyl-phenyl)-2-[4-(2-oxo-4H-benzo[d][1,3] oxazin-1-yl)-piperidin-1-yl]-acetamide hydrochloride,

[9] 2-[4-(2-oxo-4H-benzo[d][1,3]oxazin-1-yl)-piperidin-1-yl]-N-(1-oxo-indan-5-yl)-acetamide,
[10] 2-[4-(2-oxo-4H-benzo[d][1,3]oxazin-1-yl)-piperidin-1-yl]-N-(1-oxo-indan-5-yl)-acetamide hydrochloride,
[11] N-Indan-5-yl-2-[4-(2-oxo-4H-benzo[d][1,3]oxazin-1-yl)-piperidin-1-yl]-acetamide hydrochloride,
[12] N-(2-Methoxy-dibenzofuran-3-yl)-2-[4-(2-oxo-4H-benzo[d][1,3]oxazin-1-yl)-piperidin-1-yl]-acetamide hydrochloride,
[13] N-(4-Cyclohexyl-phenyl)-2-[4-(2-oxo-4H-benzo[d][1,3]oxazin-1-yl)-piperidin-1-yl]-acetamide hydrochloride,
[14] 1-{1-[2-(3,4-Dihydro-2H-quinolin-1-yl)-2-oxo-ethyl]piperidin-4-yl}-1,4-dihydro-benzo[d][1,3]oxazin-2-one hydrochloride,
[15] 2-[4-(2-oxo-4H-benzo[d][1,3]oxazin-1-yl)-piperidin-1-yl]-N-(9-oxo-9H-fluoren-3-yl)-2-phenyl-acetamide hydrochloride,
[16] 2-[4-(2-oxo-4H-benzo[d][1,3]oxazin-1-yl)-piperidin-1-yl]-N-(9-oxo-9H-fluoren-3-yl)-propionamide hydrochloride,
[17] N-(9-Ethyl-9H-carbazol-3-yl)-2-[4-(2-oxo-4H-benzo[d][1,3]oxazin-1-yl)-piperidin-1-yl]-acetamide,
[18] N-(9-Ethyl-9H-carbazol-3-yl)-2-[4-(2-oxo-4H-benzo[d][1,3]oxazin-1-yl)-piperidin-1-yl]-acetamide hydrochloride,
[19] 2-[4-(6-methyl-2-oxo-4H-benzo[d][1,3]oxazin-1-yl)-piperidin-1-yl]-N-(9-oxo-9H-fluoren-3-yl)-acetamide,
[20] 2-[4-(6-methyl-2-oxo-4H-benzo[d][1,3]oxazin-1-yl)-piperidin-1-yl]-N-(9-oxo-9H-fluoren-3-yl)-acetamide hydrochloride,
[21] N-(9-Ethyl-9H-carbazol-3-yl)-2-[4-(6-methyl-2-oxo-4H-benzo[d][1,3]oxazin-1-yl)-piperidin-1-yl]-acetamide hydrochloride,
[22] N-(4-Cyclohexyl-phenyl)-2-[4-(6-methyl-2-oxo-4H-benzo[d][1,3]oxazin-1-yl)-piperidin-1-yl]-acetamide,
[23] N-(4-Cyclohexyl-phenyl)-2-[4-(6-methyl-2-oxo-4H-benzo[d][1,3]oxazin-1-yl)-piperidin-1-yl]-acetamide hydrochloride,
[24] N-(4-benzoyl-phenyl)-2-[4-(6-methyl-2-oxo-4H-benzo[d][1,3]oxazin-1-yl)-piperidin-1-yl]-acetamide hydrochloride,
[25] N-(9-Methyl-9H-carbazol-3-yl)-2-[4-(2-oxo-4H-benzo[d][1,3]oxazin-1-yl)-piperidin-1-yl]-acetamide hydrochloride,
[26] N-(9,10-Dioxo-9,10-dihydro-anthracen-2-yl)-2-[4-(2-oxo-4H-benzo[d][1,3]oxazin-1-yl)-piperidin-1-yl]-acetamide hydrochloride,
[27] N-[4-(Ethyl-phenyl-amino)-phenyl]-2-[4-(2-oxo-4H-benzo[d][1,3]oxazin-1-yl)-piperidin-1-yl]-acetamide hydrochloride,
[28] 2-[4-(6-Methyl-2-oxo-4H-benzo[d][1,3]oxazin-1-yl)-piperidin-1-yl]-N-[4-methyl-phenyl-amino)-phenyl]-acetamide hydrochloride,
[29] 2-[4-(2-oxo-4H-benzo[d][1,3]oxazin-1-yl)-piperidin-1-yl]-N-[4-phenoxy-phenyl)-acetamide hydrochloride,
[30] N-[4-(Isopropil-phenyl-amino)-phenyl]-2-[4-(2-oxo-4H-benzo[d][1,3]oxazin-1-yl)-piperidin-1-yl]-acetamide hydrochloride,
[31] 3-[4-(2-Oxo-4H-benzo[d][1,3]oxazin-1-yl)-piperidin-1-yl]-N-(9-oxo-9H-fluoren-3-yl)-propionamide hydrochloride,
[32] 2-[4-(6-Chloro-2-oxo-4H-benzo[d][1,3]oxazin-1-yl)-piperidin-1-yl]-N-(9-ethyl-9H-carbazol-3-yl)-acetamide hydrochloride,
[33] N-(4-Chloro-phenyl)-2-[4-(2-oxo-4H-benzo[d][1,3]oxazin-1-yl)-piperidin-1-yl]-acetamide hydrochloride,
[34] 2-[4-(6-Chloro-2-oxo-4H-benzo[d][1,3]oxazin-1-yl)-piperidin-1-yl]-N-(4-chloro-phenyl)-acetamide hydrochloride,
[35] 2-[4-(8-Methyl-2-oxo-4H-benzo[d][1,3]oxazin-1-yl)-piperidin-1-yl]-N-(9-oxo-9H-fluoren-3-yl)-acetamide hydrochloride,
[36] 2-[4-(6-Chloro-2-oxo-4H-benzo[d][1,3]oxazin-1-yl)-piperidin-1-yl]-N-(9-oxo-9H-fluoren-3-yl)-acetamide hydrochloride,
[37] N-(9-Hydroxy-9H-fluoren-3-yl)-2-[4-(8-methyl-2-oxo-4H-benzo[d][1,3]oxazin-1-yl)-piperidin-1-yl]-acetamide hydrochloride,
[38] N-(9-Hydroxy-9H-fluoren-2-yl)-2-[4-(2-oxo-4H-benzo[d][1,3]oxazin-1-yl)-piperidin-1-yl]-acetamide hydrochloride,
[39] 2-[4-(6-Chloro-2-oxo-4H-benzo[d][1,3]oxazin-1-yl)-piperidin-1-yl]-N-(9-hydroxy-9H-fluoren-3-yl)-acetamide hydrochloride,
[40] N-(9-Ethyl-9H-carbazol-3-yl)-2-[4-(8-methyl-2-oxo-4H-benzo[d][1,3]oxazin-1-yl)-piperidin-1-yl]-acetamide hydrochloride,
[41] 2-[4-(8-Methyl-2-oxo-4H-benzo[d][1,3]oxazin-1-yl)-piperidin-1-yl]-N-(4-trifluoro-methyl-phenyl)-acetamide hydrochloride,
[42] 2-[4-(8-Methyl-2-oxo-4H-benzo[d][1,3]oxazin-1-yl)-piperidin-1-yl]-N-phenyl-acetamide hydrochloride,
[43] 2-[4-(2-oxo-4H-benzo[d][1,3]oxazin-1-yl)-piperidin-1-yl]-N-(4-trifluoromethyl-phenyl)-acetamide hydrochloride,
[44] 2-[4-(6-Chloro-2-oxo-4H-benzo[d][1,3]oxazin-1-yl)-piperidin-1-yl]-N-phenyl-acetamide hydrochloride,
[45] 2-[4-(6-Chloro-2-oxo-4H-benzo[d][1,3]oxazin-1-yl)-piperidin-1-yl]-N-(4-trifluoromethyl-phenyl)-acetamide hydrochloride,
[46] 2-[4-(2-oxo-4H-benzo[d][1,3]oxazin-1-yl)-piperidin-1-yl]-N-phenyl-acetamide hydrochloride,
[47] N-(4-Chloro-phenyl)-2-[4-(8-Methyl-2-oxo-4H-benzo[d][1,3]oxazin-1-yl)-piperidin-1-yl]-acetamide hydrochloride,
[48] N-(4-Cyano-phenyl)-2-[4-(2-oxo-4H-benzo[d][1,3]oxazin-1-yl)-piperidin-1-yl]-acetamide hydrochloride,
[49] N-(4-Cyano-phenyl)-2-[4-(8-methyl-2-oxo-4H-benzo[d][1,3]oxazin-1-yl)-piperidin-1-yl]-acetamide hydrochloride,
[50] 2-[4-(6-Chloro-2-oxo-4H-benzo[d][1,3]oxazin-1-yl)-piperidin-1-yl]-N-(4-cyano-phenyl)-acetamide hydrochloride,
[51] N-(4-Acethyl-phenyl)-2-[4-(2-oxo-4H-benzo[d][1,3]oxazin-1-yl)-piperidin-1-yl]-acetamide hydrochloride,
[52] 2-[4-(8-Methyl-2-oxo-4H-benzo[d][1,3]oxazin-1-yl)-piperidin-1-yl]-N-(4-phenoxy-phenyl)-acetamide hydrochloride,
[53] N-(4-Acethyl-phenyl)-2-[4-(6-chloro-2-oxo-4H-benzo[d][1,3]oxazin-1-yl)-piperidin-1-yl]-acetamide hydrochloride,
[54] N-(4-Acethyl-phenyl)-2-[4-(8-methyl-2-oxo-4H-benzo[d][1,3]oxazin-1-yl)-piperidin-1-yl]-acetamide hydrochloride,
[55] 2-[4-(6-Chloro-2-oxo-4H-benzo[d][1,3]oxazin-1-yl)-piperidin-1-yl]-N-(4-phenoxy-phenyl)-acetamide hydrochloride,

[56] N-(4-Benzoyl-phenyl)-2-[4-(8-methyl-2-oxo-4H-benzo[d][1,3]oxazin-1-yl)-piperidin-1-yl]-acetamide hydrochloride,

[57] N-(4-Benzoyl-phenyl)-2-[4-(6-chloro-2-oxo-4H-benzo[d][1,3]oxazin-1-yl)-piperidin-1-yl]-acetamide hydrochloride,

[58] N-(2-Chloro-phenyl)-2-[4-(6-methyl-2-oxo-4H-benzo[d][1,3]oxazin-1-yl)-piperidin-1-yl]-acetamide,

[59] 2-[4-(6-Methyl-2-oxo-4H-benzo[d][1,3]oxazin-1-yl)-piperidin-1-yl]-N-(2-trifluoro-methyl-phenyl)-acetamide,

[60] 2-[4-(6-Methyl-2-oxo-4H-benzo[d][1,3]oxazin-1-yl)-piperidin-1-yl]-N-phenyl-acetamide,

[61] N-(4-Cyclohexyl-phenyl)-2-[4-(8-methyl-2-oxo-4H-benzo[d][1,3]oxazin-1-yl)-piperidin-1-yl]-acetamide hydrochloride,

[62] 2-[4-(6-Chloro-2-oxo-4H-benzo[d][1,3]oxazin-1-yl)-piperidin-1-yl]-N-(4-cyclohexyl-phenyl)-acetamide hydrochloride,

[63] N-(2-Benzoyl-phenyl)-2-[4-(2-oxo-4H-benzo[d][1,3]oxazin-1-yl)-piperidin-1-yl]-acetamide hydrochloride,

[64] N-(2-Benzoyl-phenyl)-2-[4-(8-methyl-2-oxo-4H-benzo[d][1,3]oxazin-1-yl)-piperidin-1-yl]-acetamide hydrochloride,

[65] N-(2-Benzoyl-phenyl)-2-[4-(6-chloro-2-oxo-4H-benzo[d][1,3]oxazin-1-yl)-piperidin-1-yl]-acetamide hydrochloride,

[66] N-(2-Benzoyl-phenyl)-2-[4-(6-methyl-2-oxo-4H-benzo[d][1,3]oxazin-1-yl)-piperidin-1-yl]-acetamide,

[67] 2-[4-(6-Methyl-2-oxo-4H-benzo[d][1,3]oxazin-1-yl)-piperidin-1-yl]-N-(4-phenoxy-phenyl)-acetamide hydrochloride,

[68] N-(4-Acethyl-phenyl)-2-[4-(6-methyl-2-oxo-4H-benzo[d][1,3]oxazin-1-yl)-piperidin-1-yl]-acetamide hydrochloride,

[69] N-(9-Hydroxy-9H-fluoren-3-yl)-2-[4-(2-oxo-4H-benzo[d][1,3]oxazin-1-yl)-piperidin-1-yl]-acetamide hydrochloride,

[70] 2-[4-(6-Chloro-2-oxo-4H-benzo[d][1,3]oxazin-1-yl)-piperidin-1-yl]-N-(9-oxo-9H-fluoren-2-yl)-acetamide hydrochloride,

[71] 2-[4-(6-Methyl-2-oxo-4H-benzo[d][1,3]oxazin-1-yl)-piperidin-1-yl]-N-(9-oxo-9H-fluoren-2-yl)-acetamide hydrochloride,

[72] 2-[4-(8-Methyl-2-oxo-4H-benzo[d][1,3]oxazin-1-yl)-piperidin-1-yl]-N-(9-oxo-9H-fluoren-2-yl)-acetamide hydrochloride,

[73] 2-[4-(6-Chloro-2-oxo-4H-benzo[d][1,3]oxazin-1-yl)-piperidin-1-yl]-N-(9-hydroxy-9H-fluoren-2-yl)-acetamide hydrochloride,

[74] N-(9-Hydroxy-9H-fluoren-2-yl)-2-[4-(6-methyl-2-oxo-4H-benzo[d][1,3]oxazin-1-yl)-piperidin-1-yl]-acetamide hydrochloride,

[75] N-(9-Hydroxy-9H-fluoren-2-yl)-2-[4-(8-methyl-2-oxo-4H-benzo[d][1,3]oxazin-1-yl)-piperidin-1-yl]-acetamide hydrochloride,

[76] N-(9-Hydroxy-9H-fluoren-3-yl)-2-[4-(6-methyl-2-oxo-4H-benzo[d][1,3]oxazin-1-yl)-piperidin-1-yl]-acetamide hydrochloride,

[77] N-(4-Cyclohexyl-phenyl)-2-[4-(7-fluoro-2-oxo-4H-benzo[d][1,3]oxazin-1-yl)-piperidin-1-yl]-acetamide hydrochloride,

[78] N-(9-Ethyl-9H-carbazol-3-yl)-2-[4-(5-fluoro-2-oxo-4H-benzo[d][1,3]oxazin-1-yl)-piperidin-1-yl]-acetamide hydrochloride,

[79] N-(9-Ethyl-9H-carbazol-3-yl)-2-[4-(6-methoxy-2-oxo-4H-benzo[d][1,3]oxazin-1-yl)-piperidin-1-yl]-acetamide hydrochloride,

[80] N-(9-Ethyl-9H-carbazol-3-yl)-2-[4-(7-methyl-2-oxo-4H-benzo[d][1,3]oxazin-1-yl)-piperidin-1-yl]-acetamide hydrochloride,

[81] 2-[4-(5-Chloro-2-oxo-4H-benzo[d][1,3]oxazin-1-yl)-piperidin-1-yl]-N-(9-ethyl-9H-carbazol-3-yl)acetamide hydrochloride,

[82] 2-[4-(5-Fluoro-2-oxo-4H-benzo[d][1,3]oxazin-1-yl)-piperidin-1-yl]-N-(4-phenoxy-phenyl)-acetamide hydrochloride,

[83] 2-[4-(6-methoxy-2-oxo-4H-benzo[d][1,3]oxazin-1-yl)-piperidin-1-yl]-N-(9-oxo-9H-fluoren-3-yl)-acetamide,

[84] N-Dibenzofuran-2-yl-2-[4-(8-methoxy-2-oxo-4H-benzo[d][1,3]oxazin-1-yl)-piperidin-1-yl]-acetamide,

[85] 2-[4-(7-Chloro-2-oxo-4H-benzo[d][1,3]oxazin-1-yl)-piperidin-1-yl]-N-dibenzofuran-2-yl-acetamide,

[86] 2-[4-(6-Fluoro-2-oxo-4H-benzo[d][1,3]oxazin-1-yl)-piperidin-1-yl]-N-(9-oxo-9H-fluoren-3-yl)-acetamide,

[87] 2-[4-(7-Fluoro-2-oxo-4H-benzo[d][1,3]oxazin-1-yl)-piperidin-1-yl]-N-(9-hydroxy-9H-fluoren-3-yl)-acetamide,

[88] N-(9H-Carbazol-3-yl)-2-[4-(5-methyl-2-oxo-4H-benzo[d][1,3]oxazin-1-yl)-piperidin-1-yl]-acetamide,

[89] N-(9H-Carbazol-3-yl)-2-[4-(5-fluoro-2-oxo-4H-benzo[d][1,3]oxazin-1-yl)-piperidin-1-yl]-acetamide,

[90] N-(9H-carbazol-3-yl)-2-[4-(6-methoxy-2-oxo-4H-benzo[d][1,3]oxazin-1-yl)-piperidin-1-yl]-acetamide,

[91] N-(9-Ethyl-9H-carbazol-3-yl)-2-[4-(5-methoxy-2-oxo-4H-benzo[d][1,3]oxazin-1-yl)-piperidin-1-yl]-acetamide,

[92] 2-[4-(5-Methoxy-2-oxo-4H-benzo[d][1,3]oxazin-1-yl)-piperidin-1-yl]-N-(4-phenoxy-phenyl)-acetamide,

[93] N-(9-Hydroxy-9H-fluoren-3-yl)-2-[4-(7-methyl-2-oxo-4H-benzo[d][1,3]oxazin-1-yl)-piperidin-1-yl]-acetamide,

[94] N-(9-Hydroxy-9H-fluoren-3-yl)-2-[4-(8-methoxy-2-oxo-4H-benzo[d][1,3]oxazin-1-yl)-piperidin-1-yl]-acetamide,

[95] N-Dibenzofuran-2-yl-2-[4-(5-methyl-2-oxo-4H-benzo[d][1,3]oxazin-1-yl)-piperidin-1-yl]-acetamide,

[96] N-[4-(Ethyl-phenyl-amino)-phenyl]-2-[4-(7-methyl-2-oxo-4H-benzo[d][1,3]oxazin-1-yl)-piperidin-1-yl]-acetamide,

[97] N-(9H-Carbazol-3-yl)-2-[4-(8-chloro-2-oxo-4H-benzo[d][1,3]oxazin-1-yl)-piperidin-1-yl]-acetamide,

[98] N-[4-(Ethyl-phenyl-amino)-phenyl]-2-[4-(8-methoxy-2-oxo-4H-benzo[d][1,3]oxazin-1-yl)-piperidin-1-yl]-acetamide,

[99] N-(9-Hydroxy-9H-fluoren-4-yl)-2-[4-(2-oxo-4H-benzo[d][1,3]oxazin-1-yl)-piperidin-1-yl]-acetamide, or

[100] N-[4-(Hydroxy-phenyl-methyl)-phenyl-2-[4-(2-oxo-4H-benzo[d][1,3]oxazin-1-yl)-piperidin-1-yl]-acetamide.

2. A method for the preparation of a benzoxazinone-derived compound of formula (I)

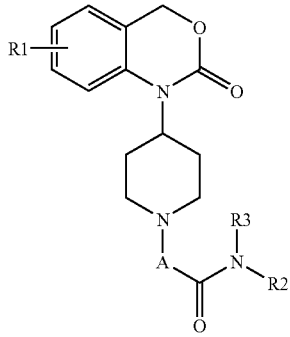

(I)

wherein:
R₁ represents hydrogen, halogen, alkoxy or a $C_1$–$C_4$ alkyl;
R₂ represents hydrogen, a $C_1$–$C_4$ alkyl, a phenyl, a benzyl or together with R₃ along with the N atom to which they are attached may be part of a five- or 6-member heterocycle;
R₃ represents bicyclic ring, tricyclic ring, phenyl substituted or phenyl substituted by a hydrocarbonated chain which together with R₂ along with the N atom to which they are attached is part of a 5 or 6-member nitrogenous heterocycle;
A represents —CHR₄— or —CHR₄—CH₂—; and
R₄ represents hydrogen, a $C_1$–$C_4$ alkyl or a phenyl;
or one of its physiologically acceptable salts, said compound being prepared by the reaction of a compound with formula (IV),

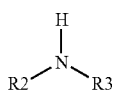

(IV)

wherein
R2 and R3 have the above-mentioned signification in formula (I) with a compound of formula (V),

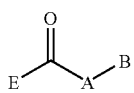

(V)

wherein
A has the above-mentioned signification in formula (I), E represents a halogen, a hydroxyl or O-acyl group, and B represents a halogen; in an inert solvent and in the presence of a base or/and auxiliaries, yielding a compound of formula (VI),

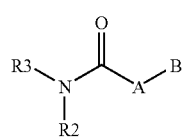

(VI)

wherein
B, A, R2 and R3 have the above-mentioned signification; and characterized by the compound's reaction with formula (VI) with an amine of formula (VII)

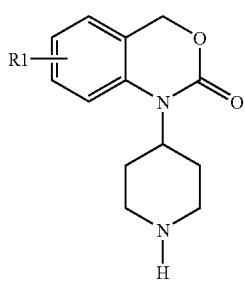

(VII)

wherein
R1 has the above-mentioned signification in formula (I), or with its corresponding salts, in inert solvents and in the presence of base and/or auxiliaries as necessary, wherein a compound of formula VII is used in preparation of compounds of formula (I), and wherein the compound of formula VII is selected from among the group:

6-methyl-1-(piperidin-4-yl)-1,4-dihydro-2H-3,1-benzoxazin-2-one,
7-methyl-1-(piperidin-4-yl)-1,4-dihydro-2H-3,1-benzoxazin-2-one,
8-methyl-1-(piperidin-4-yl)-1,4-dihydro-2H-3,1-benzoxazin-2-one,
5-chloro-1-(piperidin-4-yl)-1,4-dihydro-2H-3,1-benzoxazin-2-one,
6-chloro-1-(piperidin-4-yl)-1,4-dihydro-2H-3,1-benzoxazin-2-one,
8-chloro-1-(piperidin-4-yl)-1,4-dihydro-2H-3,1-benzoxazin-2-one,
6-fluoro-1-(piperidin-4-yl)-1,4-dihydro-2H-3,1-benzoxazin-2-one,
7-fluoro-1-(piperidin-4-yl)-1,4-dihydro-2H-3,1-benzoxazin-2-one,
5-methoxy-1-(piperidin-4-yl)-1,4-dihydro-2H-3,1-benzoxazin-2-one,
6-methoxy-1-(piperidin-4-yl)-1,4-dihydro-2H-3,1-benzoxazin-2-one,
5-hydroxy-1-(piperidin-4-yl)-1,4-dihydro-2H-3,1-benzoxazin-2-one,
6-hydroxy-1-(piperidin-4-yl)-1,4-dihydro-2H-3,1-benzoxazin-2-one,
8-hydroxy-1-(piperidin-4-yl)-1,4-dihydro-2H-3,1-benzoxazin-2-one.

3. A pharmaceutical composition comprising a pharmaceutically acceptable excipient, and at least one compound of formula (I), according to claim 1, or one of its physiologically acceptable salts.

* * * * *